US010648941B2

(12) United States Patent
Merriman et al.

(10) Patent No.: US 10,648,941 B2
(45) Date of Patent: May 12, 2020

(54) BINDING PROBE CIRCUITS FOR MOLECULAR SENSORS

(71) Applicant: Roswell Biotechnologies, Inc., San Diego, CA (US)

(72) Inventors: Barry L. Merriman, La Jolla, CA (US); Venkatesh Alagarswamy Govindaraj, San Diego, CA (US); Paul Mola, San Diego, CA (US); Tim Geiser, San Diego, CA (US); Gina Costa, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

(21) Appl. No.: 16/015,049

(22) Filed: Jun. 21, 2018

(65) Prior Publication Data

US 2019/0004003 A1 Jan. 3, 2019

Related U.S. Application Data

(63) Continuation of application No. PCT/US2018/029393, filed on Apr. 25, 2018.
(Continued)

(51) Int. Cl.
*G01N 27/327* (2006.01)
*C12Q 1/6825* (2018.01)
(Continued)

(52) U.S. Cl.
CPC ....... *G01N 27/3275* (2013.01); *C12Q 1/6825* (2013.01); *G01N 33/5438* (2013.01); *G01N 27/3276* (2013.01); *G01N 27/4145* (2013.01)

(58) Field of Classification Search
CPC ............ G01N 27/414; G01N 27/4145; G01N 27/3275; G01N 27/3276; G01N 27/3277;
(Continued)

(56) References Cited

U.S. PATENT DOCUMENTS 5,082,627 A  1/1992  Stanbro
5,194,133 A  3/1993  Clark et al.
(Continued)

FOREIGN PATENT DOCUMENTS

CN  104685066  6/2015
CN  104703700  6/2015
(Continued)

OTHER PUBLICATIONS

Bailey et al., "DNA-Encoded Antibody Libraries: A Unified Platform for Multiplexed Cell Sorting and Detection of Genes and Proteins ," J. Am. Chem. Soc. 2007, 129, 1959-1967 (Year: 2007).*
(Continued)

*Primary Examiner* — Alexander S Noguerola
(74) *Attorney, Agent, or Firm* — Snell & Wilmer L.L.P.

(57) ABSTRACT

In various embodiments a molecular circuit is disclosed. The circuit comprises a negative electrode, a positive electrode spaced apart from the negative electrode, and a binding probe molecule conductively attached to both the positive and negative electrodes to form a circuit having a conduction pathway through the binding probe. In various examples, the binding probe is an antibody, the Fab domain of an antibody, a protein, a nucleic acid oligomer hybridization probe, or an aptamer. The circuit may further comprise molecular arms used to wire the binding probe to the electrodes. In various embodiments, the circuit functions as a sensor wherein electrical signals, such as changes to voltage, current, impedance, conductance, or resistance in the circuit, are measured as targets interact with the binding probe. In various embodiments, the circuit provides a means to measure the presence, absence, or concentration of an analyte in a solution.

32 Claims, 25 Drawing Sheets

Related U.S. Application Data

(60) Provisional application No. 62/503,812, filed on May 9, 2017.

(51) Int. Cl.
  *G01N 33/543* (2006.01)
  *G01N 27/414* (2006.01)

(58) Field of Classification Search
  CPC ..... G01N 2035/00158; G01N 33/4836; C12Q 1/6813; C12Q 1/6834
  See application file for complete search history.

(56) References Cited

U.S. PATENT DOCUMENTS

| | | | |
|---|---|---|---|
| 5,366,140 A | 11/1994 | Koskenmaki et al. | |
| 5,414,588 A | 5/1995 | Barbee, Jr. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,767,687 A | 6/1998 | Geist | |
| 5,871,918 A | 2/1999 | Thorp et al. | |
| 5,881,184 A | 3/1999 | Guidash | |
| 5,982,018 A | 11/1999 | Wark | |
| 6,051,380 A | 4/2000 | Sosnowski et al. | |
| 6,060,023 A | 5/2000 | Maracas | |
| 6,094,335 A | 7/2000 | Early | |
| 6,110,354 A | 8/2000 | Saban | |
| 6,123,819 A | 9/2000 | Peeters | |
| 6,144,023 A | 11/2000 | Clerc | |
| 6,238,927 B1 | 5/2001 | Abrams et al. | |
| 6,440,662 B1 | 8/2002 | Gerwen et al. | |
| 6,464,889 B1 | 10/2002 | Lee et al. | |
| 6,506,564 B1 | 1/2003 | Mirkin et al. | |
| 6,537,747 B1 | 3/2003 | Mills, Jr. et al. | |
| 6,670,131 B2 | 12/2003 | Hashimoto | |
| 6,673,533 B1 | 1/2004 | Wohlstadter et al. | |
| 6,716,620 B2 | 4/2004 | Bashir et al. | |
| 6,749,731 B2 | 6/2004 | Kobori | |
| 6,762,050 B2 | 7/2004 | Fukushima et al. | |
| 6,764,745 B1 | 7/2004 | Karasawa et al. | |
| 6,790,341 B1 | 9/2004 | Saban | |
| 6,824,974 B2 | 11/2004 | Pisharody et al. | |
| 6,861,224 B2 | 3/2005 | Fujita et al. | |
| 6,916,614 B1 | 7/2005 | Takenaka et al. | |
| 6,958,216 B2 | 10/2005 | Kelley | |
| 7,015,046 B2 | 3/2006 | Wohlstadter et al. | |
| 7,075,428 B1 | 7/2006 | Oleynik | |
| 7,169,272 B2 | 1/2007 | Fritsch et al. | |
| 7,183,055 B2 | 2/2007 | Van Der Weide | |
| 7,189,435 B2 | 3/2007 | Tuominen et al. | |
| 7,202,480 B2 | 4/2007 | Yokoi et al. | |
| 7,208,077 B1 | 4/2007 | Albers et al. | |
| 7,276,206 B2 | 10/2007 | Augustine et al. | |
| 7,399,585 B2 | 7/2008 | Gau | |
| 7,432,120 B2 | 10/2008 | Mascolo et al. | |
| 7,470,533 B2 | 12/2008 | Xu et al. | |
| 7,507,320 B2 | 3/2009 | Hwang et al. | |
| 7,531,120 B2 | 5/2009 | Van Rijn et al. | |
| 7,579,823 B1 | 8/2009 | Ayliffe | |
| 7,691,433 B2 | 4/2010 | Kronholz et al. | |
| 7,785,785 B2 * | 8/2010 | Pourmand .............. B82Y 15/00 435/6.11 |
| 7,834,344 B2 | 11/2010 | Mascolo et al. | |
| 7,851,045 B2 | 12/2010 | Gandon et al. | |
| 7,886,601 B2 | 2/2011 | Merassi et al. | |
| 7,901,629 B2 | 3/2011 | Calatzis et al. | |
| 7,943,394 B2 | 5/2011 | Flandre et al. | |
| 8,241,508 B2 | 8/2012 | D'Urso | |
| 8,351,181 B1 | 1/2013 | Ahn | |
| 8,591,816 B2 | 11/2013 | Calatzis et al. | |
| 8,652,768 B1 | 2/2014 | Huber et al. | |
| 8,753,893 B2 | 6/2014 | Liu et al. | |
| 8,927,464 B2 | 1/2015 | Aizenberg et al. | |
| 8,940,663 B2 | 1/2015 | Iqbal et al. | |
| 9,108,880 B2 | 8/2015 | Jin et al. | |
| 9,306,164 B1 | 4/2016 | Chang et al. | |
| 9,829,456 B1 | 11/2017 | Merriman et al. | |
| 9,956,743 B2 | 5/2018 | Jin et al. | |
| 10,036,064 B2 | 7/2018 | Merriman et al. | |
| 10,125,420 B2 | 11/2018 | Jin et al. | |
| 10,151,722 B2 | 12/2018 | Jin et al. | |
| 10,508,296 B2 | 12/2019 | Merriman et al. | |
| 10,526,696 B2 | 1/2020 | Jin et al. | |
| 2002/0022223 A1 | 2/2002 | Connolly | |
| 2002/0090649 A1 | 7/2002 | Chan et al. | |
| 2002/0137083 A1 | 9/2002 | Kobori et al. | |
| 2002/0138049 A1 | 9/2002 | Allen et al. | |
| 2002/0142150 A1 | 10/2002 | Baumann et al. | |
| 2002/0142477 A1 | 10/2002 | Lewis et al. | |
| 2002/0172963 A1 | 11/2002 | Kelley et al. | |
| 2002/0184939 A1 | 12/2002 | Yadav | |
| 2003/0025133 A1 | 2/2003 | Brousseau | |
| 2003/0040000 A1 | 2/2003 | Connolly et al. | |
| 2003/0064390 A1 * | 4/2003 | Schulein .............. C12Q 1/6825 435/6.11 |
| 2003/0087296 A1 | 5/2003 | Fujita et al. | |
| 2003/0186263 A1 | 10/2003 | Frey et al. | |
| 2003/0224387 A1 | 12/2003 | Kunwar et al. | |
| 2004/0014106 A1 | 1/2004 | Patno et al. | |
| 2004/0023253 A1 | 2/2004 | Kunwar et al. | |
| 2004/0038090 A1 | 2/2004 | Faris | |
| 2004/0063100 A1 | 4/2004 | Wang | |
| 2004/0086929 A1 | 5/2004 | Weide et al. | |
| 2004/0096866 A1 | 5/2004 | Hoffman et al. | |
| 2004/0012161 A1 | 6/2004 | Chiu | |
| 2004/0146863 A1 | 7/2004 | Pisharody et al. | |
| 2004/0209355 A1 | 10/2004 | Edman et al. | |
| 2004/0209435 A1 | 10/2004 | Patridge et al. | |
| 2004/0235016 A1 | 11/2004 | Hamers | |
| 2004/0248282 A1 | 12/2004 | Sobha | |
| 2005/0029227 A1 | 2/2005 | Chapman | |
| 2005/0067086 A1 | 3/2005 | Ito et al. | |
| 2005/0151541 A1 | 7/2005 | Brinz et al. | |
| 2005/0172199 A1 | 8/2005 | Miller et al. | |
| 2005/0181195 A1 | 8/2005 | Dubrow | |
| 2005/0221473 A1 | 10/2005 | Dubin et al. | |
| 2005/0227373 A1 | 10/2005 | Flandre et al. | |
| 2005/0247573 A1 | 11/2005 | Nakamura et al. | |
| 2005/0285275 A1 | 12/2005 | Son | |
| 2005/0287589 A1 | 12/2005 | Connolly | |
| 2006/0003482 A1 | 1/2006 | Chinthakindi et al. | |
| 2006/0019273 A1 | 1/2006 | Connolly et al. | |
| 2006/0024504 A1 | 2/2006 | Nelson et al. | |
| 2006/0024508 A1 | 2/2006 | D'Urso et al. | |
| 2006/0029808 A1 | 2/2006 | Zhai et al. | |
| 2006/0051919 A1 | 3/2006 | Mascolo et al. | |
| 2006/0051946 A1 | 3/2006 | Mascolo et al. | |
| 2006/0105449 A1 | 5/2006 | Larmer et al. | |
| 2006/0105467 A1 | 5/2006 | Niksa et al. | |
| 2006/0128239 A1 | 5/2006 | Nun et al. | |
| 2006/0147983 A1 | 7/2006 | O'uchi | |
| 2006/0154489 A1 * | 7/2006 | Tornow .................. B82Y 10/00 438/745 |
| 2006/0275853 A1 | 12/2006 | Matthew et al. | |
| 2007/0026193 A1 | 2/2007 | Luzinov et al. | |
| 2007/0048748 A1 | 3/2007 | Williams et al. | |
| 2007/0140902 A1 | 6/2007 | Calatzis et al. | |
| 2007/0148815 A1 | 6/2007 | Chao et al. | |
| 2007/0184247 A1 | 9/2007 | Simpson et al. | |
| 2007/0207487 A1 | 9/2007 | Emig et al. | |
| 2007/0231542 A1 | 10/2007 | Deng | |
| 2008/0098815 A1 | 5/2008 | Merassi et al. | |
| 2008/0199657 A1 | 8/2008 | Capron et al. | |
| 2008/0199659 A1 | 8/2008 | Zhao | |
| 2009/0011222 A1 | 1/2009 | Xiu et al. | |
| 2009/0017571 A1 | 1/2009 | Nuckolls | |
| 2009/0020428 A1 | 1/2009 | Levitan | |
| 2009/0062684 A1 | 3/2009 | Gregersen et al. | |
| 2009/0152109 A1 | 6/2009 | Whitehead et al. | |
| 2009/0170716 A1 | 7/2009 | Su et al. | |
| 2009/0178935 A1 | 7/2009 | Reymond et al. | |
| 2009/0295372 A1 | 12/2009 | Krstic et al. | |

(56) References Cited

U.S. PATENT DOCUMENTS

| | | |
|---|---|---|
| 2009/0297913 A1 | 12/2009 | Zhang et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0206367 A1 | 8/2010 | Jeong et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1* | 3/2011 | Stellacci ............... B82Y 15/00 205/777.5 |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1* | 7/2011 | Kwong ............... C12Q 1/6834 506/9 |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0220046 A1 | 8/2012 | Chao |
| 2012/0258870 A1* | 10/2012 | Schwartz ............. C12Q 1/6834 506/4 |
| 2012/0286332 A1 | 11/2012 | Rothberg et al. |
| 2013/0049158 A1 | 2/2013 | Hong et al. |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0027775 A1 | 1/2014 | Quick et al. |
| 2014/0048776 A1 | 2/2014 | Huang et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0367749 A1 | 12/2014 | Bai et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0068892 A1 | 3/2015 | Ueno et al. |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0284811 A1 | 9/2016 | Yu et al. |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0168039 A1 | 6/2017 | Lindsay |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |

FOREIGN PATENT DOCUMENTS

| | | |
|---|---|---|
| CN | 108027335 | 5/2018 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| JP | 2018-522236 | 8/2018 |
| KR | 20070059880 | 6/2007 |
| KR | 20110104245 | 9/2011 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2010022107 | 2/2010 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100637 | 6/2016 |
| WO | 2016196755 | 12/2016 |
| WO | 2016210386 | 12/2016 |
| WO | WO 2016210386 A1 * | 12/2016 ............ G01N 27/26 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |

(56) References Cited

FOREIGN PATENT DOCUMENTS

| WO | 2017147187 | 8/2017 |
|---|---|---|
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |

OTHER PUBLICATIONS

Bai et al., "Review: Gas Sensors Based on Conducting Polymers," Sensors 2007, 7, 267-307 (Year: 2007).*
Antibody Structure downloaded from https://absoluteantibody.com/antibody-resources/antibody-overview/antibody-structure/ on Mar. 1, 2019 (Year: 2019).*
Khawli et al. "Charge variants in IgG1—Isolation, characterization, in vitro binding properties and pharmacokinetics in rats," Landes Bioscience 2010, pp. 613-623 (Year: 2010).*
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Notice of Allowance dated Oct. 11, 2018 in U.S. Appl. No. 15/796,080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.
PCT; International Preliminary Report on Patentability dated Aug. 14, 2018 in Application No. PCT/US2017/017231.
USPTO; Requirement for Restriction dated Jan. 17, 2017 in U.S. Appl. No. 15/336,557.
USPTO; Advisory Action dated Mar. 14, 2017 in U.S. Appl. No. 15/050,270.
USPTO; Non-Final Office Action dated May 16, 2017 in U.S. Appl. No. 15/336,557.
USPTO; Final Office Action date Dec. 30, 2016 in U.S. Appl. No. 15/050,270.
USPTO; Non-Final Office Action dated Sep. 29, 2017 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Final Office Action dated Jul. 10, 2018 in U.S. Appl. No. 15/050,270.
USPTO; Final Office Action dated Jul. 10, 2018 in U.S. Appl. No. 15/728,400.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/18950.
PCT; International Search Report and Written Opinion dated Jul. 26, 2017 in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Fink et al., "Electrical Conduction Through DNA Molecules," Nature, vol. 398, pp. 407-410, (Jan. 20, 1999).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Bechelany et al., "Synthesis Mechanisms of Organized Nanoparticles: Influence of Annealing Temperature and Atmosphere," Crystal Growth and Design, vol. 10, pp. 587-596, (Oct. 21, 2010).
H. Nishida, et al., "Self-Oriented Immobilization of DNA Polymerase Tagged by Titanium-Binding Peptide Motif," Langmuir, vol. 31, pp. 732-740, (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267, pp. 291-297, (Aug. 10, 1989) (Abstract Only).
Park, S.J. et al., "Array-Based Electrical Detection of DNA with Nanoparticle Probes," Science, vol. 295, pp. 1503-1506, (Feb. 22, 2002).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).
Ruttkowski, E. et al., "CMOS Based Arrays of Nanogaps Devices for Molecular Devices," Proceedings of 2005 5th IEEE Conference on Nanotechnology, vol. 1, pp. 438-441, (Jul. 2005) (Abstract Only).

(56) References Cited

OTHER PUBLICATIONS

Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Schrott, W. et al., "Metal Electrodes in Plastic Microfluidic Systems," Microelectronic Engineering, vol. 86, pp. 1340-1342, (Jun. 2009).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Chen, X. et al., "Electrical Nanogap Devices for Biosensing," Materials Today, vol. 13, pp. 28-41, (Nov. 2010).
Ghindilis, A. et al., "Real Time Biosensor Platforms Fully Integrated Device for Impedimetric Assays," ECS Transactions, vol. 33, pp. 59-68, (2010).
Su, Y., "Modeling and Characteristic Study of Thin Film Based Biosensor Based on COMSOL," Mathematical Problems in Engineering, Article 581063 (6 Pages), (Apr. 7, 2014).
Blossey, R., "Self-Cleaning Surfaces-Virtual Realities," Nature Materials, vol. 2(5), pp. 301-306, (May 2006).
Cassie, A.B.D. et al., "Wettability of Porous Surfaces," Transitions of the Faraday Society, vol. 40, pp. 546-551, (Jan. 1944) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Coulson S.R. et al., "Super-Repellent Composite Fluoropolymer Surfaces," The Journal of Physical Chemistry B., vol. 104(37), pp. 8836-8840, (Aug. 2000).
Gapin, A.I. et al., "CoPt Patterned Media in Anodized Aluminum Oxide Templates," Journal of Applied Physics, vol. 99(8), pp. 08G902 (1-3), (Apr. 2006).
Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al2O3 Nanowires Having Superhydrophobic Characteristics," Nano: Brief Reports and Reviews, vol. 5(2), pp. 89-95, (Apr. 2010) (Abstract Only).
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for DNA Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella Pnuemophila," Anal. Chem., vol. 79, pp. 4050-4055, (Jun. 1, 2007).

Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-523, (May 10, 2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report dated Nov. 9, 2018 in Application No. PCT/US2018/048873.
PCT; Written Opinion dated Nov. 9, 2018 in Application No. PCT/US2018/048873.
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Van Gerwin et al., "Nanoscaled Interdigitated Electrode Arrays for Biochemical Sensors," Sensors and Actuators B, vol. 49, pp. 73-80, (1998).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Javey et al., "Layer-By-Layer Assembly of Nanowires for Three-Dimensional, Multifunctional Electronics," Nano Letters, vol. 7, pp. 773-777, (2007).
Fan et al., "Detection of MicroRNAs Using Target-Guided Formation of Conducting Polymer Nanowires in Nanogaps," Journal of the American Chemical Society, vol. 129, pp. 5437-5443, (2007).
Kitsara et al., "Single Chip Interdigitated Electrode Capacitive Chemical Sensor Arrays," Sensors and Actuators B, vol. 127, pp. 186-192, (2007).
Xu et al., "Fabrication of Complex Metallic Nanostructures by Nanoskiving," American Chemical Society Nano, vol. 1(3), pp. 215-227, (2007).
Berdat et al., "Label-Free Detection of DNA with Interdigitated Micro-Electrodes in a Fluidic Cell," Lab on a Chip, vol. 8, pp. 302-308, (2008).
Dickey et al., "Electrically Addressable Parallel Nanowires with 30 NM Spacing from Micromolding and Nanoskiving," Nano Letters, vol. 8(12), pp. 4568-4573, (2008).
Singh et al., "3D Nanogap Interdigitated Electrode Array Biosensors," Analytical and Bioanalytical Chemistry, vol. 397, pp. 1493-1502, (2010).
Bhura, "3D Interdigitated Electrode Array (IDEA) Biosensor for Detection of Serum Biomarker," Master Thesis, Portland State University, 68 Pages, (2011).

(56) References Cited

OTHER PUBLICATIONS

Ino et al., "Addressable Electrode Array Device with IDA Electrodes for High-Throughput Detection," Lab on a Chip, vol. 11, p. 385-388, (2011).
Bonilla et al., "Electrical Readout of Protein Microarrays on Regular Glass Slides," Analytical Chemistry, vol. 83, pp. 1726-1731, (2011).
Ahn et al., "Electrical Immunosensor Based on a Submicron-Gap Interdigitated Electrode and Gold Enhancement," Biosensors and Bioelectronics, vol. 26, pp. 4690-4696, (2011).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Chen et al., "Fabrication of Submicron-Gap Electrodes by Silicon Volume Expansion for DNA-Detection," Sensors and Actuators A, vol. 175, pp. 73-77, (2012).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Botsialas et al., "A Miniaturized Chemocapacitor System for the Detection of Volatile Organic Compounds," Sensors and Actuators B, Chemical, vol. 177, pp. 776-784, (2013).
Sanguino et al., "Interdigitated Capacitive Immunosensors with PVDF Immobilization Layers," IEEE Sensors Journal, vol. 14(4), pp. 1260-1265, (Apr. 2014).
Van Megan et al., "Submicron Electrode Gaps Fabricated by Gold Electrodeposition at Interdigitated Electrodes," Key Engineering Materials, vol. 605, pp. 107-110, (2014).
MacNaughton et al., "High-Throughput Heterogeneous Integration of Diverse Nanomaterials on a Single Chip for Sensing Applications," PLOS One, vol. 9(10), e111377, 7 Pages, (2014).
Kitsara et al., "Small-Volume Multiparametric Electrochemical Detection at Low Cost Polymeric Devices Featuring Nanoelectrodes," SPIE, vol. 9518, 9 Pages, (2015).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Han et al., "Redox Cycling in Nanopore-Confined Recessed Dual-Ring Electrode Arrays," Journal of Physical Chemistry C, vol. 120, pp. 20634-20641, (2016).
Okinaka et al., ""Polymer" Inclusions in Cobalt-Hardened Electroplated Gold," Journal the of Electrochemical Society, vol. 125, p. 1745, (1978).
Braun et al., "DNA-Templated Assembly and Electrode Attachment of a Conducting Silver Wire," Letters to Nature, vol. 391(6669), pp. 775-778, (Feb. 1998).
Chen et al., "Electrochemical Approach for Fabricating Nanogap Electrodes with Well Controllable Separation," Applied Physics Letters, vol. 86, pp. 123105.1-123105.3, (2005).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Iqbal et al., "Direct Current Electrical Characterization of ds-DNA in Nanogap Junctions," Applied Physics Letter, vol. 86, p. 153901-1-153901-3, (Apr. 2005).

Liu et al., "Controllable Nanogap Fabrication on Microchip by Chronopotentiometry," Electrochimica Acta, vol. 50, pp. 3041-3047, (2005).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reichert et al., "Driving Current Through Single Organic Molecules," Physical Review Letters, vol. 88(17), pp. 176804-1-176804-4, (Apr. 2002).
Reed et al., "Conductance of a Molecular Junction Reports," Science, vol. 278, pp. 252-254, (Oct. 1997).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Kraft, "Doped Diamond: A Compact Review on a New, Versatile Electrode Material," International Journal of Electrochemistry, vol. 2, pp. 355-385, (May 2007).
USPTO; Non-Final Office Action dated Feb. 26, 2019 in U.S. Appl. No. 15/050,270.
USPTO; Final Office Action dated Mar. 1, 2019 in U.S. Appl. No. 15/979,135.
USPTO; Non-Final Office Action dated Mar. 7, 2019 in U.S. Appl. No. 15/944,356.
USPTO; Final Office Action dated Apr. 15, 2019 in U.S. Appl. No. 16/015,028.
Schaefer et al., "Stability and Dewetting Kinetics of Thin Gold Films on Ti, TiOx, and ZnO Adhesion Layers," Acta Materiala, vol. 61, pp. 7841-7848, (2013).
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, in U.S. Appl. No. 16/152,190.
USPTO; Non-Final Office Action dated Jun. 25, 2019 in U.S. Appl. No. 15/979,135.
USPTO; Final Office Action dated Jul. 10, 2019 in U.S. Appl. No. 15/050,270.
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
PCT; International Search Report and Written Opinion dated Jan. 18, 2019 in Application No. PCT/US2018/055264.
CN; Notice of the First Office Action dated Sep. 2, 2019 in Chinese Application No. 201680049272.8.
EP; European Search Report dated Jan. 30, 2019 in Application No. EP16815467.2.
EP; European Search Report dated Aug. 2, 2019 in Application No. EP16885434.7.
EP; European Search Report dated Aug. 2, 2019 in Application No. EP17745026.9.
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Henry et al., "Microcavities Containing Individually Addressable Recessed Microdisk and Tubular Nanoband Electrodes," Journal of the Electrochemical Society, vol. 146(9), pp. 3367-3373, (1999).
Lin et al., "An Addressable Microelectrode Array for Electrichemical Detection," Analytical Chemistry, vol. 80, pp. 6830-6833, (2008).
Thompson, "Solid-State Dewetting of Thin Films," Department of Materials Science and Engineering, vol. 42, pp. 399-434, (2012).

(56) References Cited

OTHER PUBLICATIONS

USPTO; Notice of Allowance dated Oct. 23, 2019 in U.S. Appl. No. 16/250,929.
USPTO; Non-Final Office Action dated Oct. 24, 2019 in U.S. Appl. No. 16/073,706.
USPTO; Notice of Allowance dated Nov. 8, 2019 in U.S. Appl. No. 16/015,028.
USPTO; Non-Final Office Action dated Nov. 5, 2019 in U.S. Appl. No. 16/015,049.
USPTO; Notice of Allowance dated Dec. 11, 2019 in U.S. Appl. No. 15/979,135.
USPTO; Notice of Allowance dated Jan. 6, 2020 in U.S. Appl. No. 15/050,270.
USPTO; Non-Final Office Action dated Jan. 10, 2020 in U.S. Appl. No. 16/076,673.
EP; European Search Report dated Oct. 24, 2019 in Application No. 17757146.

* cited by examiner

BINDING PROBE CIRCUITS FOR MOLECULAR SENSORS

CROSS-REFERENCE TO RELATED APPLICATIONS

This application is a continuation of PCT Application No. PCT/US18/29393, filed on Apr. 25, 2018 entitled "Binding Probe Circuits for Molecular Sensors," which claims priority to and the benefit of U.S. Provisional Patent Application Ser. No. 62/503,812 filed May 9, 2017 and entitled "Binding Probe Circuits for Molecular Sensors," the disclosure of which are incorporated herein by reference in their entirety.

FIELD

The present disclosure is generally directed to molecular sensors and more particularly to molecular sensors in which a binding probe closes the circuit between two electrodes.

BACKGROUND

The broad field of molecular electronics was introduced in the 1970s by Aviram and Ratner. Molecular electronics achieves the ultimate scaling down of electrical circuits by using single molecules as circuit components. Molecular circuits comprising single molecule components can function diversely as switches, rectifiers, actuators and sensors, depending on the nature of the molecule. Of particular interest is the application of such circuits as sensors, where molecular interactions provide a basis for single molecule sensing. In particular, informative current changes could include an increase, a decrease, a pulse, or other time variation in the current.

Notwithstanding the achievements in the field of molecular electronics, new molecular circuits that can function as molecular sensors are still needed. In particular, the need still exists for improved single molecule systems that can yield molecular information with greater signal-to-noise ratios such that signals truly indicative of molecular interactions are distinguishable from non-informative noise.

SUMMARY

In various embodiments, single molecule binding probe-based circuits are disclosed wherein a single binding probe molecule is directly connected to a positive and negative electrode to form the circuit. These circuits are capable of yielding highly informative signals of binding activity. These improved signals have greater signal-to-noise levels such that the signals are more distinguishable from noise, and these improved signals include features that carry detailed information about the engagement between the binding probe and the target binding partner.

In various embodiments, a molecular sensor comprises a binding probe-based molecular circuit (conductive pathway) such as described herein. Such a sensor is usable to sense the binding of a target to the binding probe, and thereby identify the target as being present in a given test solution. This provides the basis of using such a sensor to detect the presence or absence of a target molecule, or to obtain information on the concentration of a target molecule, in a test solution. Consequently, a binding of a target molecule to the binding probe active site is sensed as an electrical change in the circuit, such as a change in the voltage, current, impedance, conductance or resistance of the circuit.

In various embodiments of the present disclosure, a molecular circuit is disclosed. The circuit comprises: a positive electrode; a negative electrode spaced apart from the positive electrode; and a binding probe connected to both the positive and negative electrodes to form a conductive pathway between the positive and negative electrodes.

In various aspects, the binding probe of the circuit may comprise a first wiring point connected to the positive electrode and a second wiring point connected to the negative electrode.

In various aspects, the circuit may further comprise at least one arm molecule having two ends, one end bonded to the binding probe and the other end bonded to at least one of the electrodes, wherein the at least one arm molecule acts as an electrical wire between the binding probe and at least one of the electrodes.

In various aspects, the at least one arm molecule may be selected from the group consisting of a double stranded oligonucleotide, a peptide nucleic acid duplex, a peptide nucleic acid-DNA hybrid duplex, a protein alpha-helix, a graphene-like nanoribbon, a natural polymer, a synthetic polymer, and an antibody Fab domain.

In various aspects, at least one of the electrodes is connected to an internal structural element of the binding probe.

In various aspects, the internal structural element may be selected from the group consisting of an alpha-helix, a beta-sheet, and a multiple of such elements in series.

In various aspects, at least one of the electrodes may be connected to the binding probe at a location of the binding probe capable of undergoing conformational changes.

In various aspects, at least one arm molecule may comprise a molecule having tension, twist or torsion dependent conductivity.

In various aspects, the binding probe may be connected to both the positive and negative electrodes from more than two locations in the binding probe.

In various aspects, the binding probe may comprise an antibody Fab binding domain.

In various aspects, the binding probe may comprise an aptamer.

In various aspects, the binding probe may comprise a nucleic acid oligomer hybridization probe.

In various aspects, a molecular sensor comprises a circuit further comprising a positive electrode; a negative electrode spaced apart from the positive electrode; and a binding probe comprising an antibody Fab binding domain connected to both the positive and negative electrodes to form a conductive pathway between the positive and negative electrodes, wherein the sensor is usable to sense information on the presence of, or concentration of a corresponding antibody antigen in a test solution.

In various aspects, a molecular sensor comprises a circuit further comprising a positive electrode; a negative electrode spaced apart from the positive electrode; and a binding probe comprising an aptamer connected to both the positive and negative electrodes to form a conductive pathway between the positive and negative electrodes, wherein the sensor is usable to sense information on the presence of, or concentration of a target molecule of the aptamer in a test solution.

In various aspects, a molecular sensor comprises a circuit further comprising a positive electrode; a negative electrode spaced apart from the positive electrode; and a binding probe comprising a nucleic acid oligomer hybridization probe connected to both the positive and negative electrodes to form a conductive pathway between the positive and negative electrodes, wherein the sensor is usable to sense information on the presence of, or concentration of a target DNA or RNA molecule in a test solution.

In various aspects, binding probes comprising an antibody Fab binding domain, an aptamer, or a nucleic acid oligomer hybridization probe may be engineered to have additional charge groups that variably influence the conductive pathway as the binding probe engages with a target.

In various aspects of a circuit comprising a positive electrode; a negative electrode spaced apart from the positive electrode; and a binding probe connected to both the positive and negative electrodes to form a conductive pathway between the positive and negative electrodes, the connection between the binding probe and at least one of the positive electrode and negative electrode may comprise at least one of a native cysteine, a genetically engineered cysteine, a genetically engineered amino acid with a conjugation residue, or a genetically engineered peptide domain comprising a peptide that has a conjugation partner.

In various aspects, molecular circuits disclosed herein may further comprise a gate electrode.

In various aspects, a method of detecting the concentration of an analyte in a solution comprises providing a circuit comprising a positive electrode; a negative electrode spaced apart from the positive electrode; and a binding probe capable of binding the analyte connected to both the positive and negative electrodes to form a conductive pathway between the positive and negative electrodes; initiating at least one of a voltage or a current through the circuit; exposing the circuit to the solution for a period of time; and measuring electrical signals through the circuit as the binding probe engages with the analyte, wherein the electrical signals are processed to identify features that provide information on the concentration of the analyte in the solution.

In various aspects, a method of molecular detection comprises providing a circuit comprising a positive electrode; a negative electrode spaced apart from the positive electrode; and a binding probe connected to both the positive and negative electrodes to form a conductive pathway between the positive and negative electrodes; initiating at least one of a voltage or a current through the circuit; exposing the circuit to at least one of: a buffer of reduced ionic strength, specific applied voltage on the primary electrodes, a gate electrode voltage, or voltage spectroscopy or sweeping applied to the primary electrodes or gate electrode; and measuring an electrical change in the circuit.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures:

DETAILED DESCRIPTION

Figure 1:
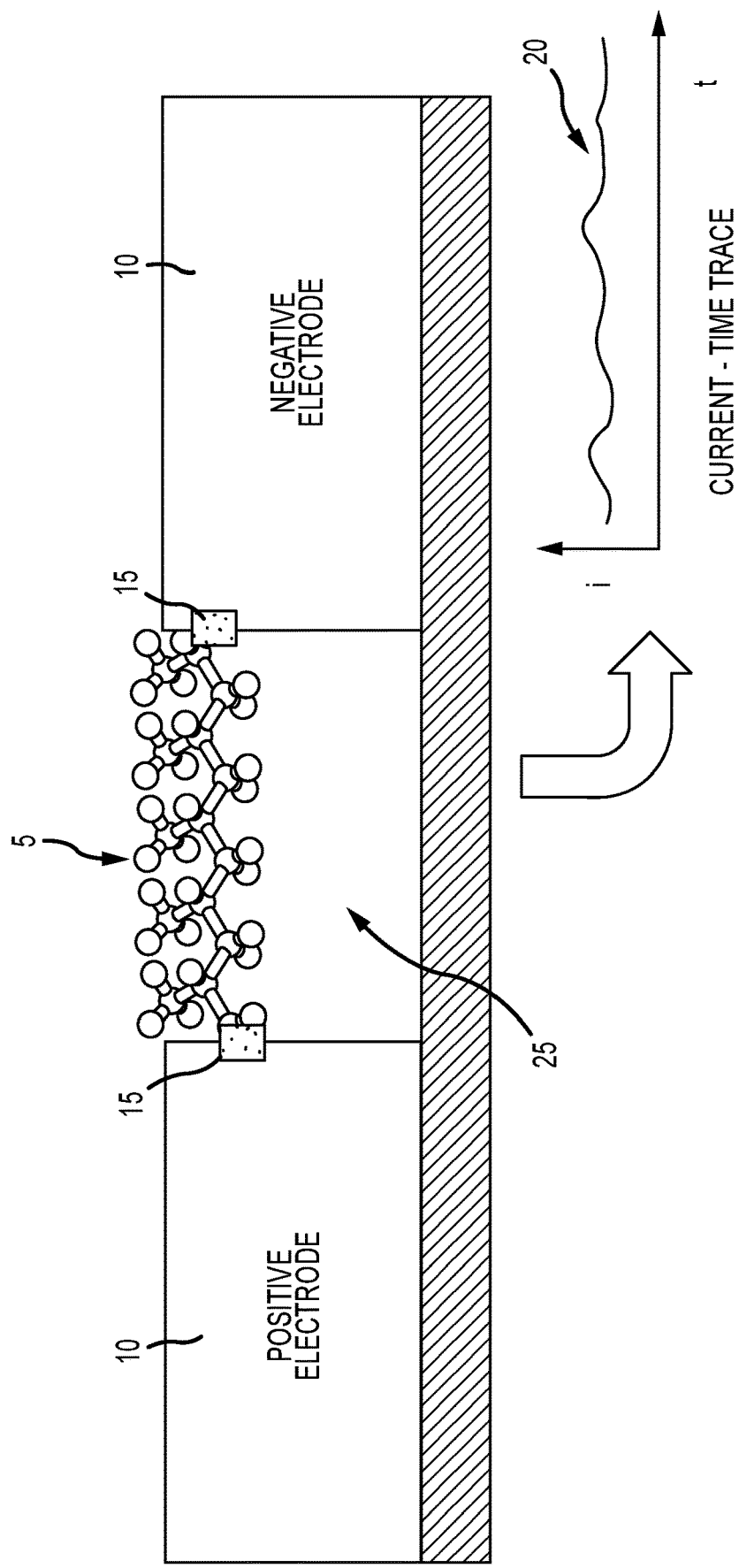
FIG. 1 illustrates the general concept of a molecular electronic circuit.

The detailed description of exemplary embodiments herein makes reference to the accompanying drawings, which show exemplary embodiments by way of illustration and their best mode. While these exemplary embodiments are described in sufficient detail to enable those skilled in the art to practice the inventions detailed herein, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, a molecular circuit is disclosed. The molecular circuit comprises: a positive electrode; a negative electrode spaced apart from the positive electrode; and a binding probe connected to both the positive and negative electrodes to form a conductive pathway between the positive and negative electrodes. In various examples, the binding probe comprises a first wiring point connected to the positive electrode and a second wiring point connected to the negative electrode.

DEFINITIONS AND INTERPRETATIONS

As used herein, the term "binding probe" means a molecule that acts to bind to another molecule, or a set of molecules, in a specific fashion. Common binding probe molecules used in biotechnology include single stranded DNA oligos, single stranded RNA oligos, either of which act as hybridization binding probes, aptamers (composed of peptides, DNA, RNA, PNA, LNA, etc.) which bind small molecule targets, and antibodies and various derivatives of antibodies that comprise the antibody Fab binding domains, which bind their cognate antigens or specific antigen epitopes. Common binding probes in biology include the broad family of immunoglobulin proteins, such as IgG, IgY, IgM, scFV, hcIgF, IgNAR, and other immunoglobulins, including native forms as well as genetically modified forms of these protein molecules. Such immunoglobulins bind to whatever epitope they have been defined to target, as produced by either in vivo immune responses, or direct engineering of the binding loops of such molecules, via the methods of synthetic biology. The binding domains of these immunoglobulins, or genetically modified forms thereof, such as Fab domains, are also binding probes.

Other well-known binding probes include the avidin family of proteins, which bind to biotin as a target. In certain embodiments, a binding probe comprises a genetically modified form of an avidin, such as Streptavidin, Neutravidin, Avidin, or any other member of the avidin family of proteins.

Binding probes for use herein may comprise single or multiple protein amino acid chains, such as IgG or antibody Fab domains which have heavy and light protein chains. Binding probes herein are optionally complexed with other types of molecules, such as RNA, polysaccharides, etc. Binding probes may bind a single target at one time, or may bind multiple targets at one time, such as in the case of IgG, which can bind two epitopes at one time. Aptamer binding probes are often comprised of RNA or peptides. Binding probes for nucleic acid hybridization are a special class of probes in which the probe oligomer binds and forms a helical duplex with the cognate binding target, and where such binding is based on the well-known complementary base pairings between the nucleic acid bases, A:T, C:G, and their various forms present in DNA, RNA, PNA, LNA or other nucleic acid analogs (designate generally as XNA), which undergo similar complementary or degenerate pairings.

As used herein, the term "target" for a binding probe refers to any of the molecules or molecular components that the binding probe specifically binds. For example, in the specific case an IgG antibody, the epitopes of the antibody are the targets, as are larger molecules or complexes that contain these epitopes.

As used herein, the term "buffer" for a binding probe refers to a solution in which the binding probe is viable and functional. Such a buffer may typically comprise salts, detergents, and surfactants, singly or in various combinations, as well as specific cofactors, along with the target molecules. Such a buffer may have its composition modified from standard forms, such as to enhance signal properties in a sensor exposed to the buffer.

As used herein, the term "electrode" means any structure that can act as an efficient source or sink of charge carriers. Most commonly these would be metal or semiconductor structures, such as those used in electronic circuits. A pair of spaced apart electrodes herein may comprise a source and drain electrode pair. In various embodiments of the present disclosure, a binding probe-based molecular circuit may further comprise a gate electrode. When present, a "gate" electrode is used to apply a voltage rather than transfer charge carriers. Thus it supports accumulation of charge carriers to produce a local electric field, but is not intended to pass current. A gate electrode will be electrically isolated from the primary conduction paths of the circuit by some form of insulating layer or material.

As used herein, the term "conjugation" means any of the wide variety of means of physically attaching one molecule to another, or to a surface or particle. Such methods typically involve forming covalent or non-covalent chemical bonds, but may also rely on protein-protein interactions, protein-metal interactions, or chemical or physical adsorption via intermolecular (Van der Waals) forces. There is a large variety of such methods known to those skilled in the art of conjugation chemistry. Common conjugation methods herein include, but are not limited to, thiol-metal bonds, maleimide-cysteine bonds, material binding peptides such as gold binding peptides, and click chemistries.

As used herein, the term "initiating," in the context of an electrical parameter, is intended to be broader than the concept of "applying" an electrical value. For example, an electrical current may be initiated in a circuit. Such initiating of a current may be the result of applying a voltage to the circuit, but may be from other actions to the circuit besides applying a voltage. Further, a voltage may be initiated in a circuit. Such initiating of a voltage may be the result of applying a current to the circuit, but may be from other actions to the circuit besides applying an electrical current. In other examples, a voltage or a current may be initiated in one portion of a circuit as the result of applying a voltage or a current to the overall circuit. In a non-limiting example, a flow of electrons initiated from a negative to a positive electrode in a circuit of the present disclosure may be controlled by the voltage applied to the gate electrode of the circuit.

In various embodiments of the present disclosure, a molecular sensor comprises a binding probe connected to both a positive and a negative electrode to complete a circuit. Interactions of the binding probe with various targets are detectable as changes in the current or other electrical parameter measured across the circuit. The present molecular sensor differs from the general concept of a molecular electronic circuit in that the binding probe is directly "wired" to both the positive and negative electrodes rather than bonded to a molecular bridge molecule that spans the gap between the electrodes to complete a circuit.

In various aspects of the disclosure, at least one of a voltage or a current is initiated in a binding probe-based molecular circuit. When a target interacts with the binding probe, electrical changes in the circuit are sensed. These electrical changes, or informative electrical signals, may include current, voltage, impedance, conductivity, resistance, capacitance, or the like. In some examples, a voltage is initiated in the circuit and then changes in the current through the circuit are measured as targets interact with the binding probe. In other examples, a current is initiated in the circuit, and changes to voltage in the circuit are measured as targets interact with the binding probe. In other examples, impedance, conductivity, or resistance is measured. In examples wherein the circuit further comprises a gate electrode, such as positioned underneath the gap between the positive and negative electrodes, at least one of a voltage or a current may be applied to the gate electrode, and voltage, current, impedance, conductivity, resistance, or other electrical change in the circuit may be measured as targets interact with the binding probe.

FIG. 1 illustrates the general concept of a molecular electronic circuit having a bridge molecule 5 attached to and bridging the gap 25 between electrodes 10, as well as some type of conjugation group 15 or other mechanism that binds the molecule to the electrodes (depicted as small shaded squares). FIG. 1 further illustrates that a current, (i), may pass through this molecule and be measured versus time, (t), as shown in the inset plot 20.

Figure 2:
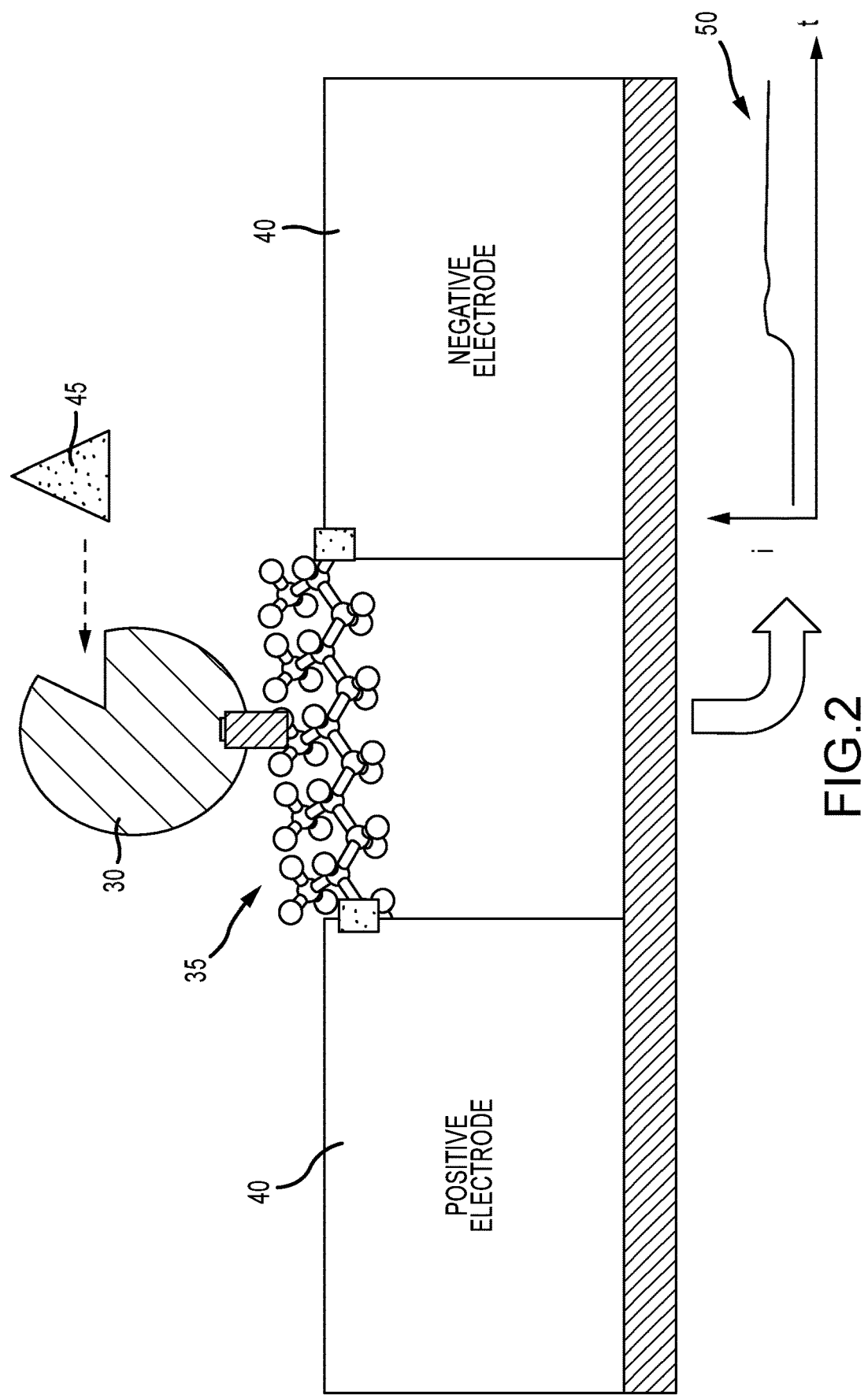
FIG. 2 illustrates the general concept of engaging a binding probe to a molecular electronic circuit, such as to act as a sensor of the probe binding to its target.

FIG. 2 illustrates a molecular electronic sensor in which a binding probe 30 is conjugated to the molecular bridge component 35 spanning the electrodes 40, wherein monitoring the current provides a way of sensing the bonding of the binding probe to its target molecule 45 when exposed to a suitable buffer solution. In such a sensor system, the local charge perturbations that result from the target engaging with the binding probe perturb charge transport through the primary bridge component, and are thus registered as a change in conductivity or current versus time, as indicated by the step-up change in the current (i) vs. time (t) current plot inset 50 in FIG. 2.

In contrast to the general molecular circuit concept as depicted in FIGS. 1 and 2, in various embodiments of the present disclosure a molecular sensor comprises a single binding probe molecule directly wired into the circuit path, such that all electrical current passing through the molecular circuit must flow through the binding probe. Thus the binding probe is an essential conduction path in the circuit, like an electronic component on a circuit board. The present concept is illustrated generally in FIG. 3, which shows a binding probe 55 connected between two molecular arms 60. By forcing all current in the circuit to pass through the binding probe, the current carriers are forced to pass closer to the precise location of electrochemical interactions between the binding probe and its target 65, thereby causing such interactions to have greater impact on the current carriers, and, in turn making the overall current more sensitive to the details of these interactions. This is illustrated schematically by the current versus time, (i vs. t), plot inset 70 in FIG. 3, wherein the current step is shown to be much larger than that produced by the configuration of FIG. 2, and also includes additional features not present in a current versus time plot such as depicted in FIG. 2. The higher current step provides improved signaling. Related methods and embodiments herein promote improved signaling of binding probe-based molecular sensors. Further, the configuration of the binding probe as an essential conduction path is fundamentally different from the common configuration of FIG. 2, in which there are many conduction paths that do not pass through the binding probe, and where potentially none of the charge carriers actually traverse the binding probe, and where there is no means provided to direct charge carriers to pass near key active sites within the binding probe.

In various embodiments, the binding probe may be coupled to both positive and negative electrodes at two or more points, such as to ensure that charge carriers traversing the molecular structure pass into and out of the binding probe.

Figure 3:
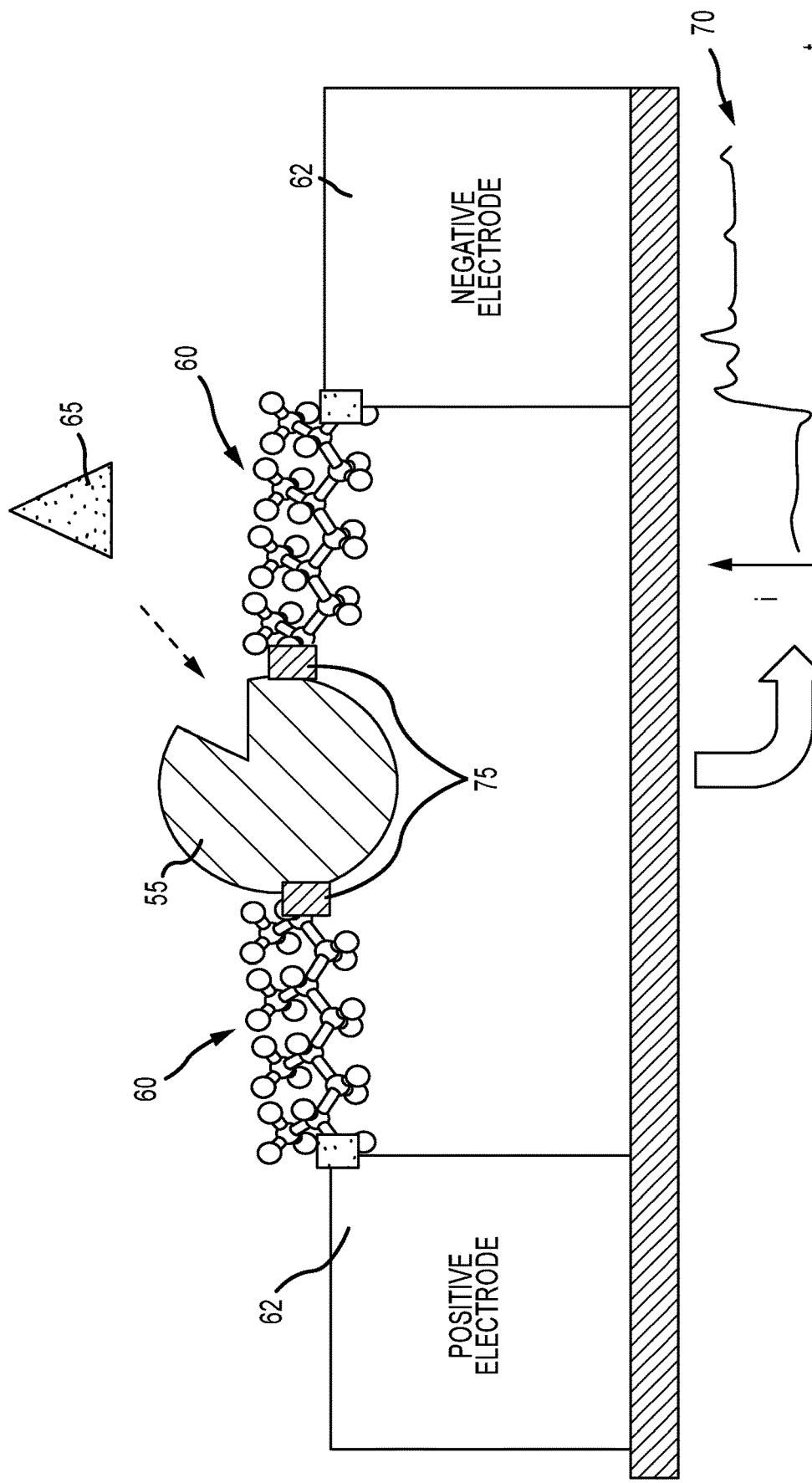
FIG. 3 illustrates a binding probe that is wired directly into the current path, in accordance with various embodiments.

As shown in the embodiment of FIG. 3, two molecular arms are conjugated 75 to the binding probe to provide physical anchors and entry and exit paths for the current through the binding probe. Such arms may comprise any convenient molecule that provides a conducting connection or semi-conducting connection between the binding probe and the electrodes 62. Further, molecular arms may provide spanning length extensions, to help span a larger electrode gap that is wider than the 3D structure of the binding probe. Such arms may also provide the advantage of keeping the binding probe away from contacting either of the electrodes where unfavorable or damaging interactions may occur with the electrodes, such as a denaturing or other destructive adsorption to an electrode. Such arms may also provide for more compatible or efficient coupling to the electrodes, such as by coupling to the electrodes via chemical groups that are not readily found or made available on the binding probe. For example, in one specific embodiment, the electrode comprises gold and the molecular arm includes a thiol group, such that the arm couples to the gold electrode via well-known thiol-gold binding. Thus the molecular arm accomplishes the binding while the binding probe may not have such available thiol groups. Or, in another embodiment, the arms may present a click-chemistry binding group, for coupling to electrodes that are derivatized with the cognate binding partners for the click chemistry.

In various embodiments, molecular arms comprise some form of conjugation to the binding probe, as well as their conjugations or couplings to the electrodes. Many conjugation chemistries can be employed for this purpose. In a non-limiting example, such conjugation comprises chemical crosslinking, which can preferentially couple suitable chemical groups on the arms to amino acid residues on the binding probe. In various embodiments, a maleimide group on the arm couples to a surface cysteine on the binding probe. In other aspects, genetically modified versions of a binding probe may be created and employed, such as binding probe comprising specific amino acids or protein domains engineered into their amino acid structure that provide specific conjugation sites. For example, cysteine amino acids engineered at specific sites on the binding probe provide for the attachment point of arms that present a maleimide group. Two such cysteine sites conjugate to two maleimide derivatized arms to produce a configuration such as that shown in FIG. 3. In this case, one or more native cysteines that would provide competing arm binding sites may be "engineered out" of the amino acid sequence. If all such sites cannot be removed, it is possible to use various purification methods from synthetic chemistry to isolate desired binding probe-arm conjugates from unwanted configurations. In other variations, genetic methods are used to engineer into the amino acid sequence of the binding probe amino acids comprising residues that uniquely conjugate to a cognate group on the arms. This variation includes cases where non-standard amino acids are employed, such as amino acids modified to present a click-chemistry group, via protein expression systems that use a modified genetic code and modified transfer RNAs to put non-native amino acids at specific sequence sites in an expressed protein component of a binding probe.

In other embodiments, a peptide domain that specifically binds with a cognate group on the arms is engineered into the sequence of a protein component of a binding probe. In one such embodiment, a peptide that is an antigen to an antibody is engineered into the binding probe, and the Fab binding domain of the antibody is used on the arms. One such embodiment is to use the FLAG peptide motif DYKDD, and any suitable ANTI-FLAG Fab domain. Any other peptide antigens and their cognate Fab domains can similarly be used to conjugate arms to specific sites in an engineered protein, by engineering the peptide antigen into the desired conjugation sites on the binding probe. Other such peptide domains make use of the SPY-TAG/SPY-CATCHER protein-protein binding system, by engineering either the SPY-TAG domain or the SPY-CATCHER domain into a protein component of the binding probe, and placing the cognate domain in the arms. When engineering such peptide binding domains into the binding probe, another embodiment includes adding short linker peptide sequences flanking the target peptide, such as to enhance the availability of the domain for binding. Such short linkers may comprise short glycine and serine rich linkers, as are known to those skilled in the art of protein engineering, including, but not limited to, the linker amino acid sequences G, GS, GSG, GGSG, etc.

In various examples, the arm molecules comprise any molecules that provide for conduction of charge carriers into and out of the binding probe. In certain embodiments, such arms comprise molecular wires from the many forms known in field of molecular electronics, functionalized with suitable conjugation and binding groups for wiring to electrodes and binding probe. In various aspects, such arms may comprise single stranded DNA, double stranded DNA, peptide nucleic acids (PNAs), peptides, peptide alpha-helices, antibodies, Fab domains of antibodies, carbon nanotubes, graphene nanoribbons, natural polymers, synthetic polymers, other organic molecules with p-orbitals for electron delocalization, or metal or semiconductor nanorods or nanoparticles. In further embodiments, the arms may comprise double stranded DNA with thiol-bearing groups at one end, and maleimide at the other end that couples to the binding probe, or a peptide alpha-helix with a cysteine or gold binding peptide at one termini and a maleimide at the other end that couples to the binding probe, or a graphene nanoribbon with thiol-bearing groups at one end, and a maleimide bearing group at the other end that couples to the binding probe. In certain embodiments, two arm molecules used to couple a binding probe to two electrodes are identical molecules, and in other embodiments, the two arm molecules are different molecules. In some examples, there may be a "positive electrode" arm and a "negative electrode" arm, providing for oriented binding of a binding probe to the corresponding "positive" and "negative" electrodes in FIG. 3.

Figure 4:
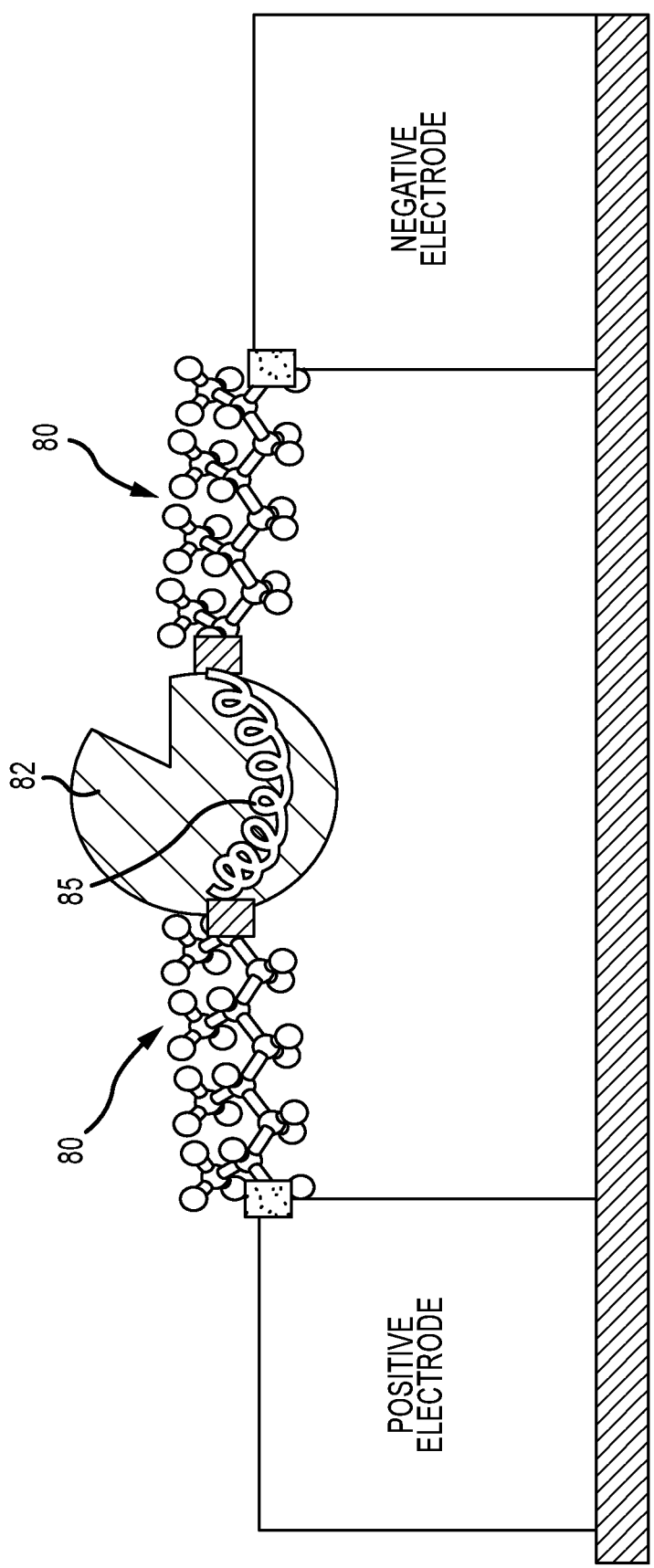
FIG. 4 illustrates a binding probe wired directly into the current path, with the connection made to an internal alpha-helix structure within the probe, in accordance with various embodiments.
Figure 5:
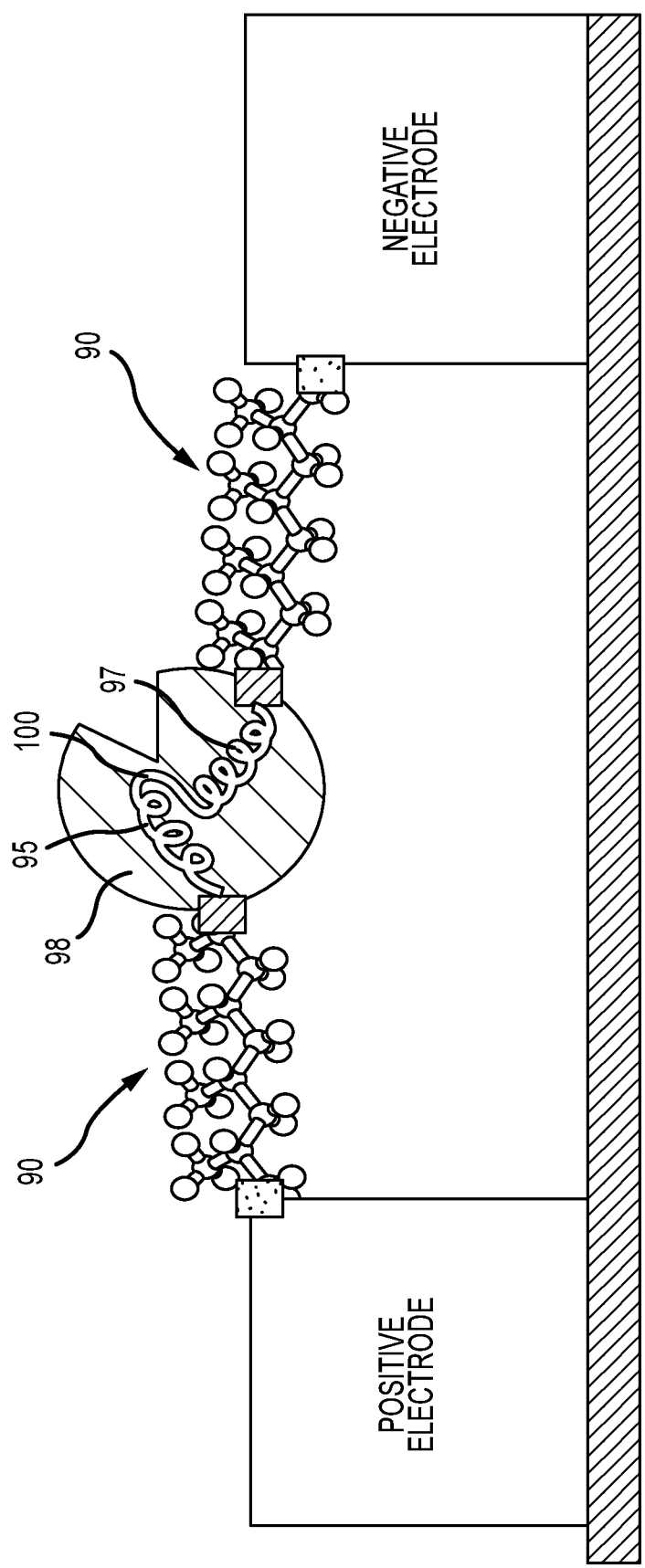
FIG. 5 illustrates a binding probe wired directly into the current path, with the connection made to a series of two or more internal alpha-helix structures in series within the probe, in accordance with various embodiments.
Figure 6:
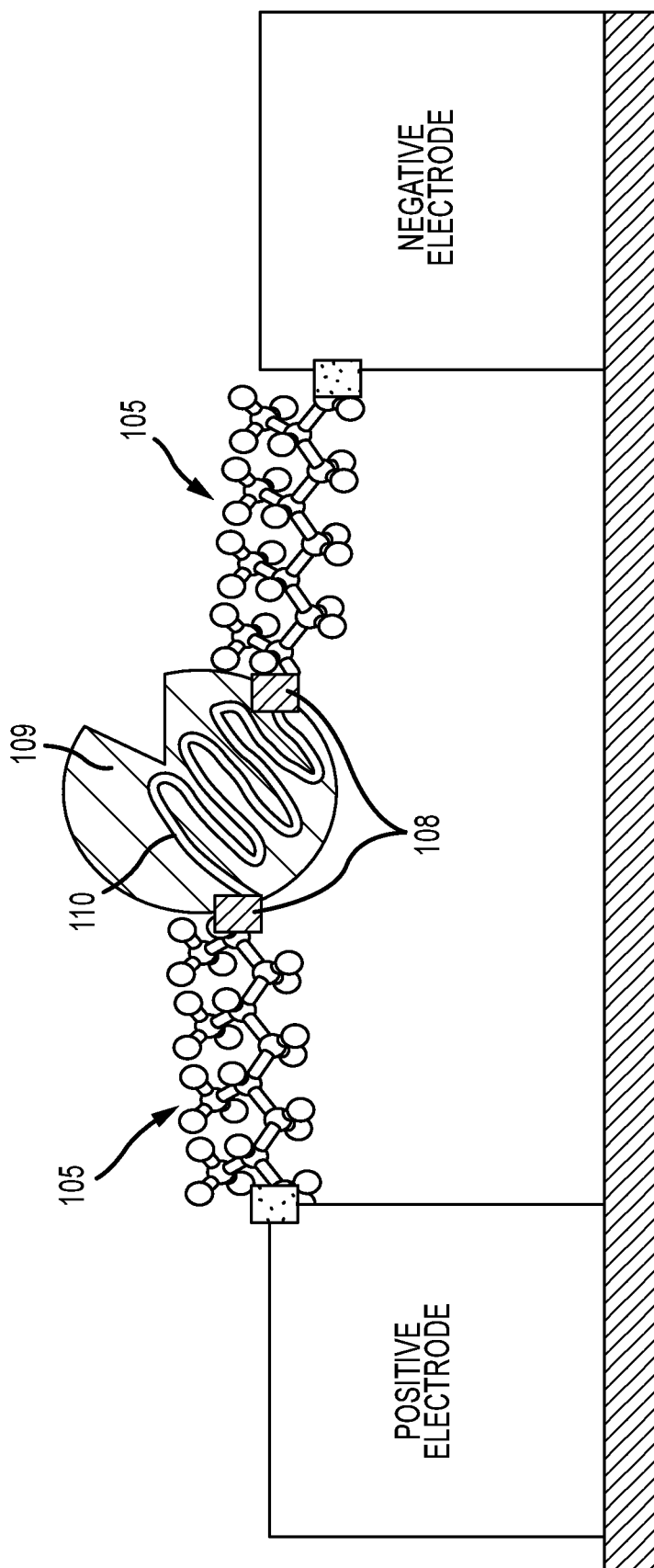
FIG. 6 illustrates a binding probe wired directly into the current path, with the connection made to an internal beta-sheet structure within the probe, in accordance with various embodiments.

In various embodiments, arm conjugation points connect directly to specific structural elements within the binding probe. A non-limiting example is illustrated in FIG. 4, where the two molecular arms 80 are shown wired directly to an alpha-helix structure 85 in the binding probe 82. Such structural elements provide preferential conduction paths through the binding probe. Direct wiring to natural conduction paths in the binding probe can guide current closer to active regions of interest within the binding probe, such as target binding pockets, and may thereby provide for further enhanced current signals, or current signals that carry more information on binding probe-target interactions. For example, one embodiment is shown in FIG. 4, where the arms wire directly to an alpha-helix that spans between two points on or near the surface of the binding probe. Another example is shown in FIG. 5, where the arms 90 wire directly to two alpha-helices (the first alpha helix 95 and the second alpha helix 97) that appear in series internally in the binding probe 98, with a single connecting loop 100 separating them. Yet another embodiment is shown in FIG. 6, where the arms 105 wire directly to two points 108 on a beta-sheet 110 internal to the binding probe 109.

In general, a protein component of a binding probe will have a 3D structure that includes well known secondary structural elements such as alpha-helices and beta-sheets. These are primarily hydrogen bonded structures that can provide discrete conduction paths through the body of the binding probe, to the extent that current carriers, such as electrons, may efficiently hop along such structures, or along the hydrogen bonds that define such structures, with less resistance than otherwise hopping or tunneling off such structures. These structures provide preferential conduction paths that will channel charge carriers, and by selecting such structures, charge is forced to pass close to active regions of the binding probe, and current-based sensing of the activity will be improved. Having the arms directly connected to such structures, or within a small number of amino acids of the termini of such structures, the current flowing along these desirable paths is maximized, and thus the desirable signals that come from the current along such paths is maximized. In this way, current going elsewhere within the binding probe is minimized, and thus the noise from probing these less informative regions is also minimized.

In various examples, the wiring can be to such structures that appear in the binding probe "in series," such as for example, two alpha-helices in series as indicated in FIG. 5, or a beta-sheet in series with an alpha-helix, or three successive alpha-helices. In general, each successive element in series appears in the binding probe primary amino acid sequence as separated from the previous element by a small number of amino acids, such 0, 1, 2, or up to approximately 10 amino acids, which typically form a connecting loop in the secondary structure. Wiring of elements in series may also be achieved by wiring to structures that are not contiguous in the primary amino acid sequence of the protein in the binding probe, but are nonetheless spatially contiguous and in conductive contact, and form a preferred conduction path, owing to hydrogen bonding, salt bridges, disulfide bridges, or other types of molecular interaction that establish secondary, tertiary or quaternary protein structure and that can provide a clearly defined and favorable conduction path from one structural element (beta-sheet, alpha-helix) to another. These structural elements of interest for wiring, either in isolation or in series, are most evident when examining the 3D structure of the proteins involved, as can be observed from the crystal structures, and in particular, by examination of the protein structures obtained by X-ray or NMR crystallography. This useful form of structural information is illustrated by the Fab domain structure shown in FIG. 12, and illustrated in FIG. 13 as it relates to preferred wiring such a Fab binding probe into a circuit.

Figure 7:
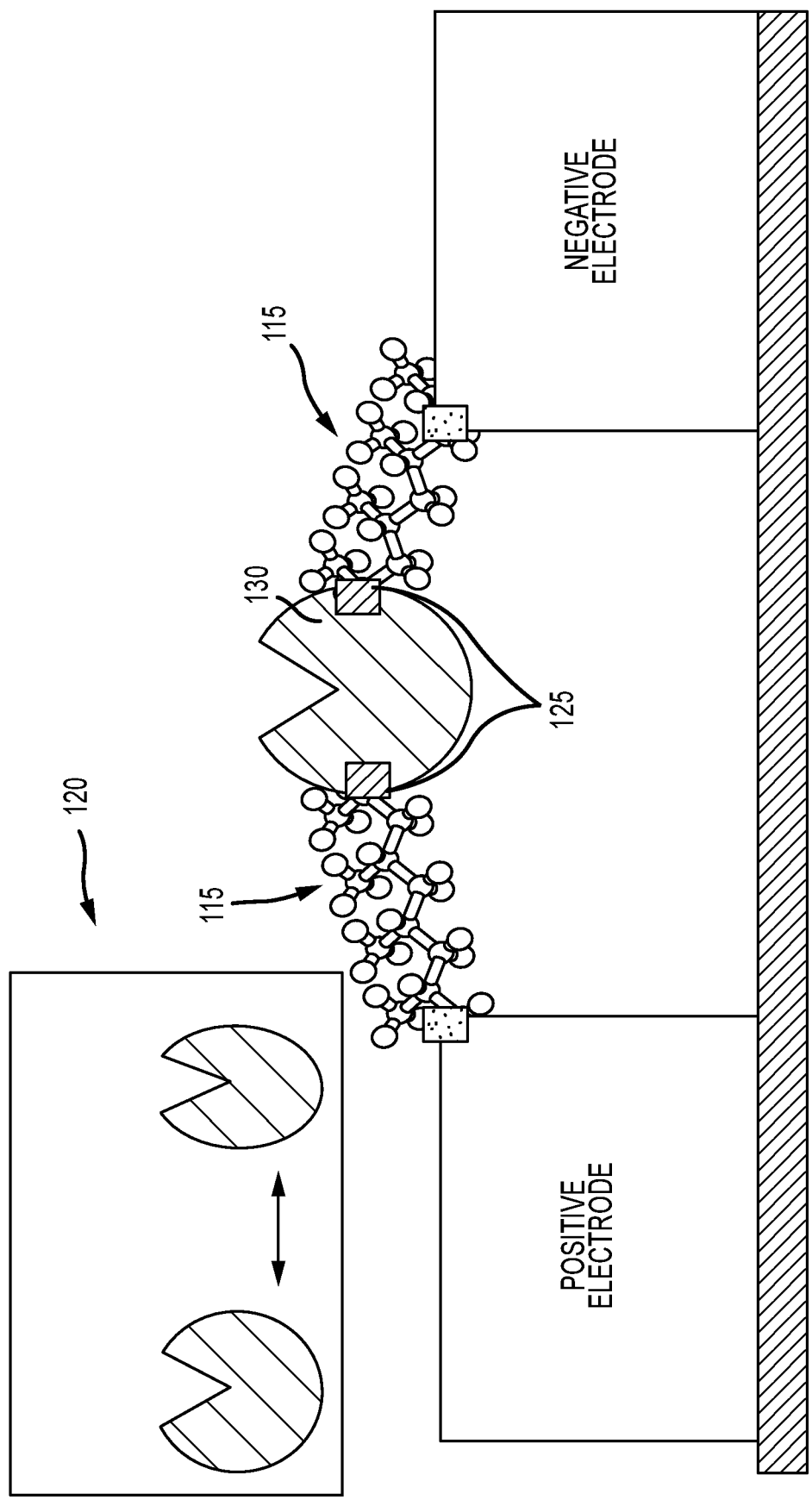
FIG. 7 illustrates a binding probe wired directly into the current path, such that connections are made to points of conformational change in the probe, to induce tension changes into the circuit during binding activity.

In other embodiments, the arms 115 are wired to points 125 on the binding probe 130 that undergo conformation changes or relative motion during binding probe binding, such as illustrated in FIG. 7. In this case, the arms are wired to two points that are indicated as having relative motion during binding probe activity that results in conformation changes of the binding probe (as shown by the inset 120). This configuration can enhance signaling by several means. First, such motions can change the tension in the arms, and it is known that tension changes in molecules can change their conductivity, thus the motion may be transduced via tension into a change in conductivity of the arms, which consequently shows up in the current signals. In this way, the current may contain information about the conformational changes in the binding probe. Second, similarly, this configuration can cause tension in the binding probe as it changes conformation, and thus alter conductivity of the binding probe. Since the binding probe is an essential current path, the conformation changes would transduce into current changes, and thereby represent conformation information in the sensing current. This configuration could also enhance signaling by altering the conformational changes of the binding probe, which may in some situations lead to an enhanced signal, for either a native binding probe, or one engineered to specifically benefit from such conformation-sensitive wiring. In one embodiment, a binding probe is engineered to have extended regions that undergo greater conformational change or relative motion (e.g. as demonstrated by extending the length of the two tips of the binding probe indicated in FIG. 7), so as to enhance the range of motion, and therefore the range of tension changes in the arms and binding probe.

In other aspects, conformational changes in the binding probe, such as when induced binding occurs between the binding probe and a substrate, are translated into a twist, torque or rotation of at least one arm, and that twist, torsion or rotation alters the conductivity of the arm. One such example is an arm comprising an organic polymer further comprising polycyclic aromatic rings, such as polythiophene or polyphenylene, whereby previously lined up p-orbitals are rotated out of alignment by C—C bond rotation when the arm is twisted, torqued or rotated in response to a binding probe conformational change. When the arm is twisted, torqued or rotated, the electrons have impeded delocalization through the π-system of the organic polymer. In certain embodiments, such impeded flow may act on only a subset of the charge carriers, depending on, for example, the polarization or other quantum state of the charge carrier, such as spin polarization of an electron charge carrier, or the momentum or energy state of the charge carrier.

Figure 8:
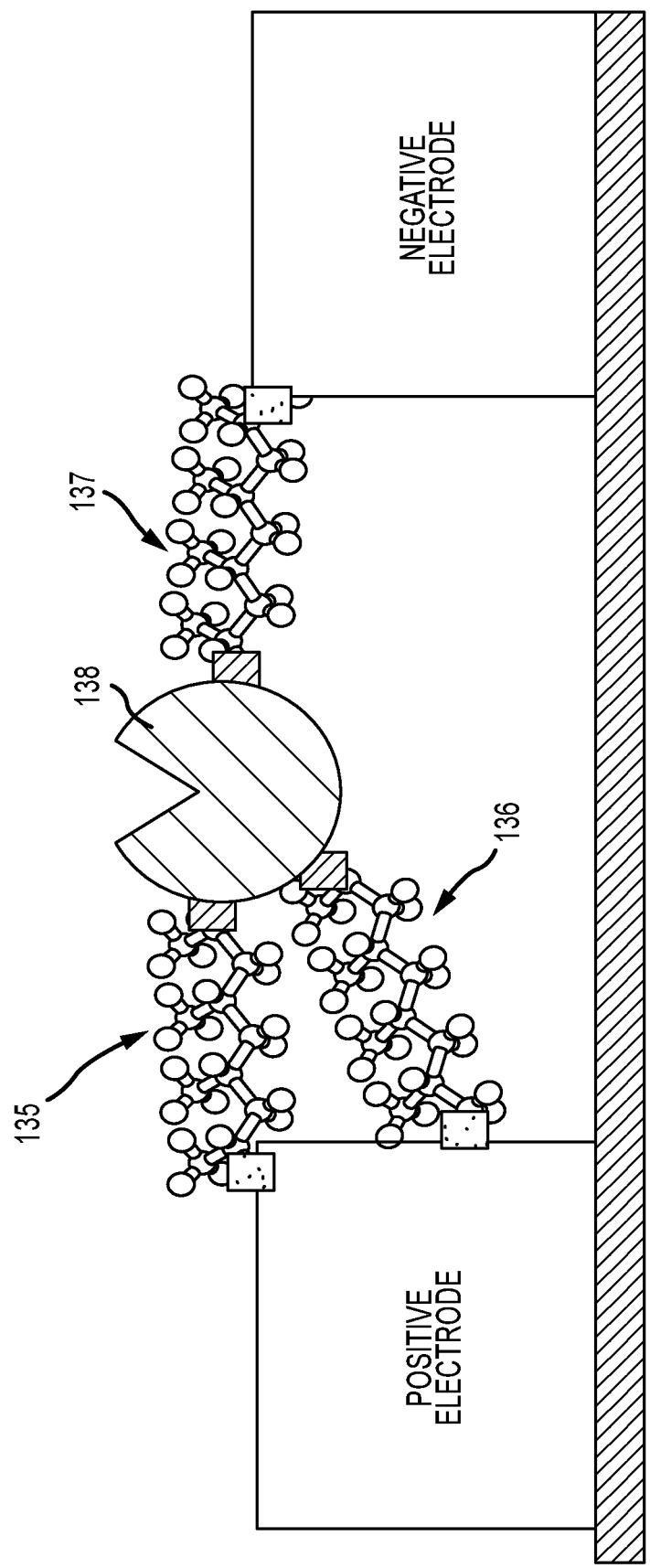
FIG. 8 illustrates a binding probe wired directly into the current path, with additional connections made to stabilize the position of the probe.

Another example is illustrated in FIG. 8, wherein the molecular sensor circuit comprises more than two arms, for example, three arms (the first arm 135, the second arm 136, and the third arm 137). The benefits to using additional binding probe wiring points and associated arms include addition of other desirable conduction paths through the binding probe 138, and increasing the overall conduction through the binding probe. Such additional arms may also provide stabilization, impose a spatial orientation (such as to orient an active site of a binding probe in a certain direction), or otherwise reduce physical degrees of freedom or conformational entropy, which may improve sensing by reducing the variability in conduction that comes from the system having more accessible conformations. Such additional arms may be conductive, but they can also be insulating if they are present primarily to provide stability, orientation, or reduction in spatial degrees of freedom. Such additional arms may connect to the electrode, or to other portions of the structure, such as to a substrate supporting the electrodes. Such arms may connect to additional electrodes in a system comprising more than two electrodes, including the case of a system with a gate electrode, such as a buried gate electrode. Connection to a gate electrode may refer to connection to the conductive portion of the gate, or connection to the insulating layer that separates actual conductive gate from the circuit, or, in the case of a buried gate, the surface layer above the buried gate, such as the connection to the surface illustrated in FIG. 16.

Figure 9:
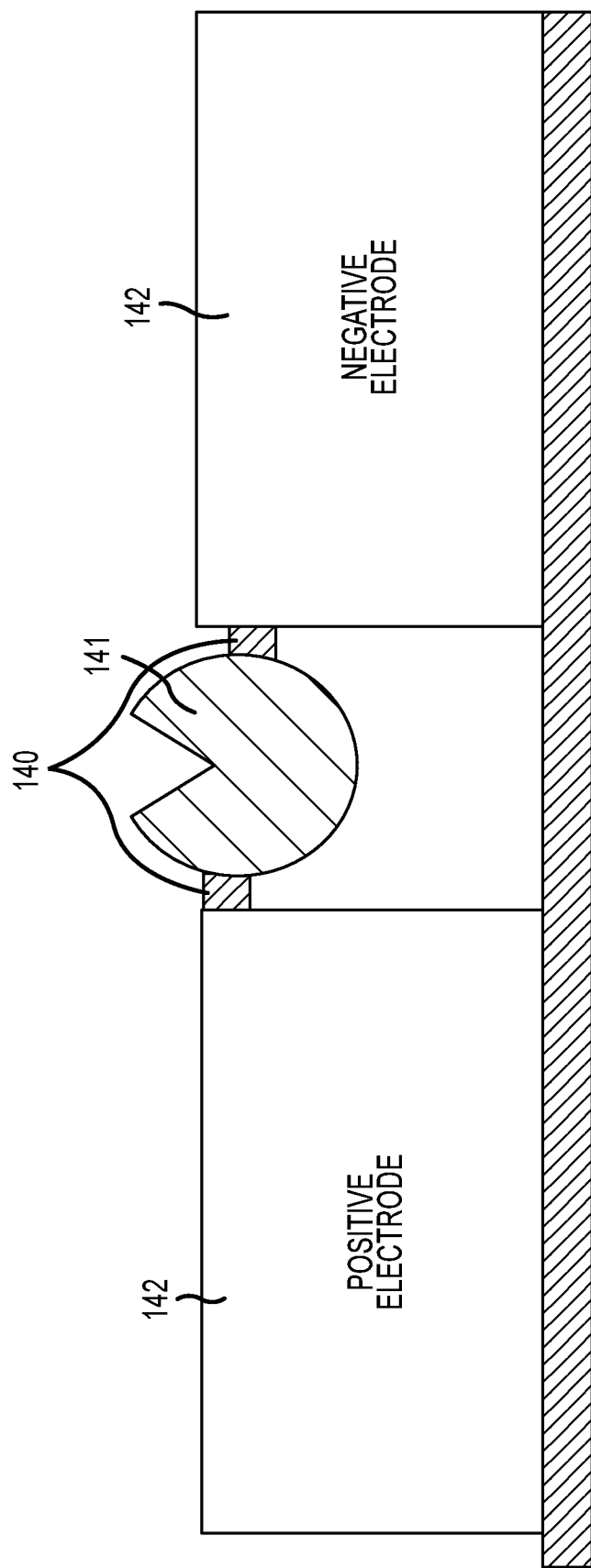
FIG. 9 illustrates a schematic of a binding probe directly wired into the current path of a circuit, in accordance with various embodiments, wherein the probe directly couples to the electrodes without the use of arm molecules.

As illustrated in FIG. 9, the binding probe may be connected to the electrodes 142 directly, as an essential conduction path, without the use of arm molecules. In this case, groups on the binding probe 141 directly couple 140 to the electrodes. Or, in another embodiment, one wiring connection comprises direct coupling to the binding probe, the other via an arm molecule. The advantages of this arm-less configuration include minimizing the length of the conduction path, since the parts of the conduction path outside of the binding probe can be sources of unwanted noise, resistance or capacitance. The considerations above for the case of wiring with arms generally also apply to the special cases of an arm-less configuration as well as the configuration of a single arm combined with direct binding probe coupling. Specifically, in embodiments lacking arms, the binding probe may still be wired via internal structures, or at points of conformational change.

A sensor comprising a directly wired binding probe as an essential conduction path may have its signal performance enhanced through various environmental factors. For example, the choice of buffer, buffer additives, temperature and applied voltage may be modulated to improve the signal quality. In particular, since binding probes may complex with various cofactors that modulate their kinetics, and the salt levels in the buffer also impact binding probe kinetics, as does temperature, these factors may be used to improve signaling performance. In addition, the overall ionic strength of the buffer solution defines the Debye length in the solution, that is the distance over which electric fields extend in solution, and can impact the extent to which current carriers passing through the binding probe are influenced by the charge distributions of the binding probe and substrate, and thus buffer ionic strength or total salt concentration is another means of influencing or enhancing the signaling.

The applied driving voltage may be optimized to improve the signaling from a binding probe wired as an essential conduction path. Based on energy barriers within the binding probe, certain voltages may lead to improved signaling performance. In addition to an applied voltage, various embodiments may also have a gate electrode, such as a buried gate below the lower substrate indicated in FIG. 3, such that voltages applied to the gate electrode further modulate the signaling properties of the binding probe circuit. Certain embodiments may employ voltage spectroscopy, wherein the driving or gate voltages are swept through a range of values, and the signal of interest is in the response from this sweep, which contains information on the interaction between the binding probe and its binding targets.

Figure 10:
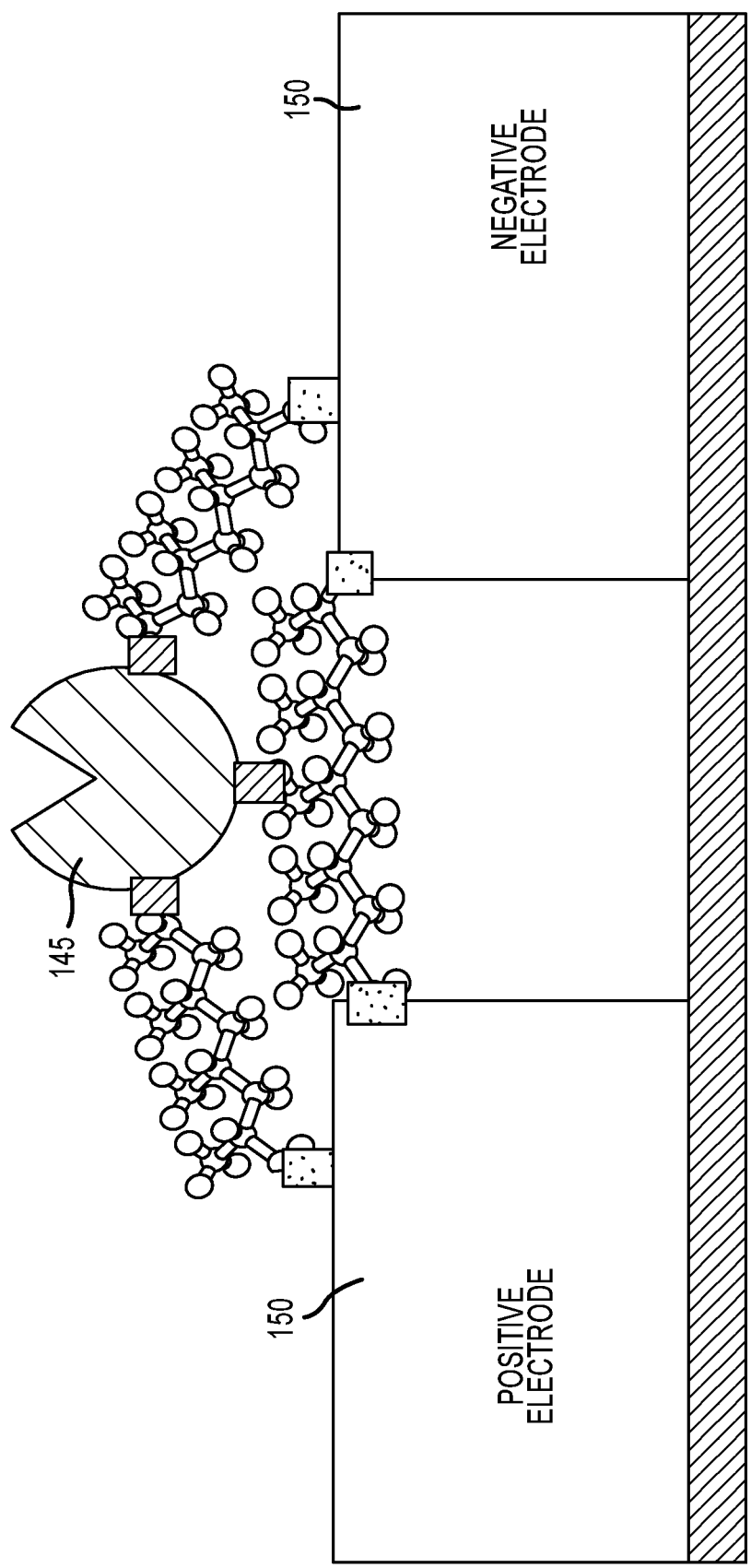
FIG. 10 illustrates a schematic of a binding probe directly wired by two points of contact into a circuit, as well as also having a one-point conjugation to a molecular wire, utilizing one pair of electrodes to measure the combined conduction, in accordance with various embodiments.
Figure 11:
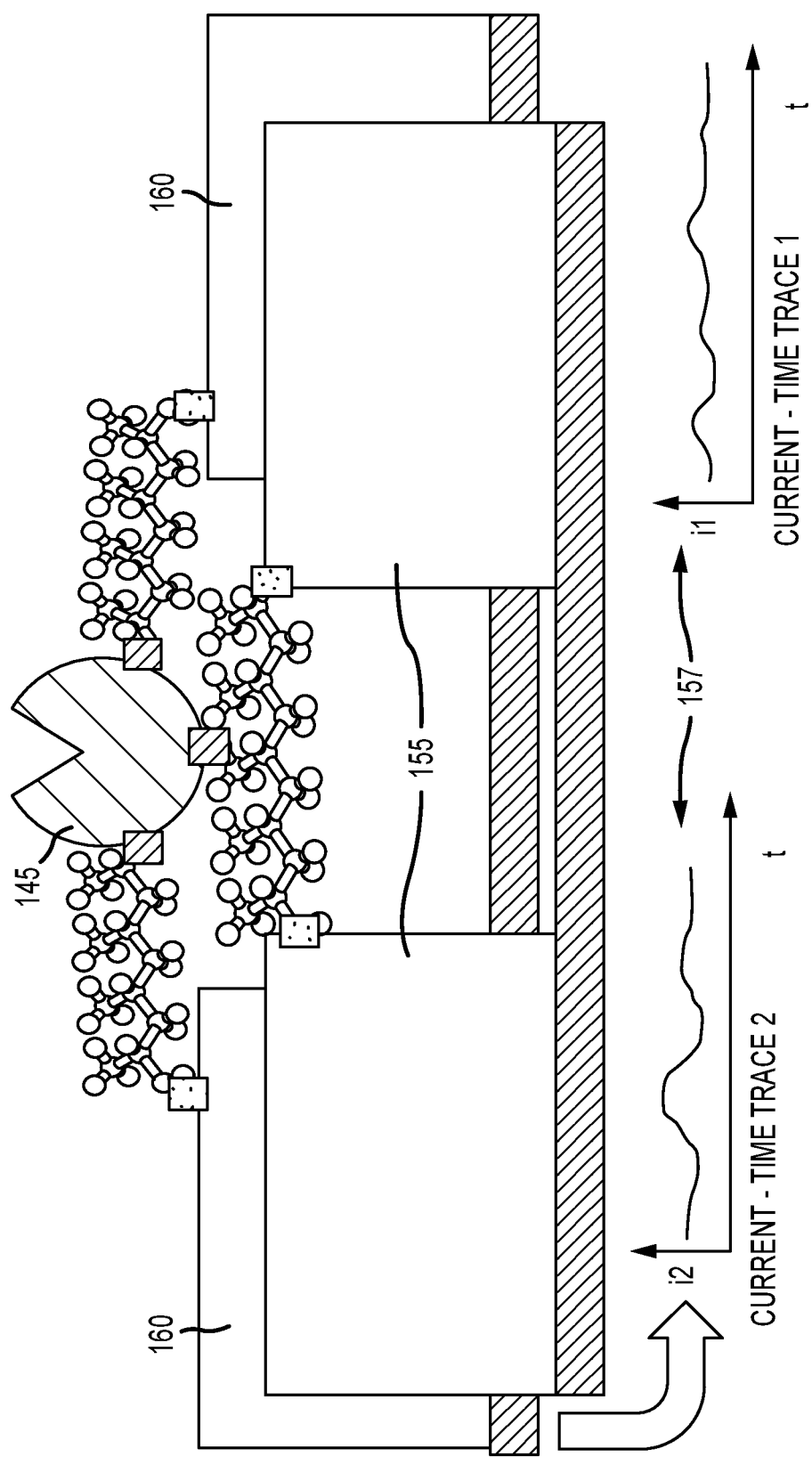
FIG. 11 illustrates a schematic of a binding probe directly wired by two points of contact into a circuit, as well as also having a one-point conjugation to a molecular wire, utilizing two pairs of electrodes to measure these two modes of conduction independently, in accordance with various embodiments.

In general, the molecular circuit sensors of the present disclosure comprise the wiring of a binding probe with at least two points of electrical contact, so as to make the binding probe an essential conduction path, in contrast to the configuration of FIG. 2. Two-point wiring of the binding probe may be combined with a conjugation to a molecular wire, as shown in FIGS. 10 and 11. In these embodiments, the current can be both driven through the binding probe 145, for sensing, and the binding probe can also modulate current through the other molecular wire, as an additional sensing mode. In FIG. 10, these conduction modes are monitored by a single electrode pair 150, and combine to produce a single current, whereas in FIG. 11, these two conduction modes can be monitored by two separate electrode pairs (a first electrode pair 155 and a second electrode pair 160), producing two current measurements 157. In certain embodiments, the sensor may comprise a binding probe wired up with two or more points of contact as a conduction path, in conjunction with additional sensor configuration features. Wiring the binding probe at two points, with input and output electrical contacts, can provide enhanced signaling. Other possible and non-limiting configurations are illustrated in FIGS. 10 and 11.

Figure 12:
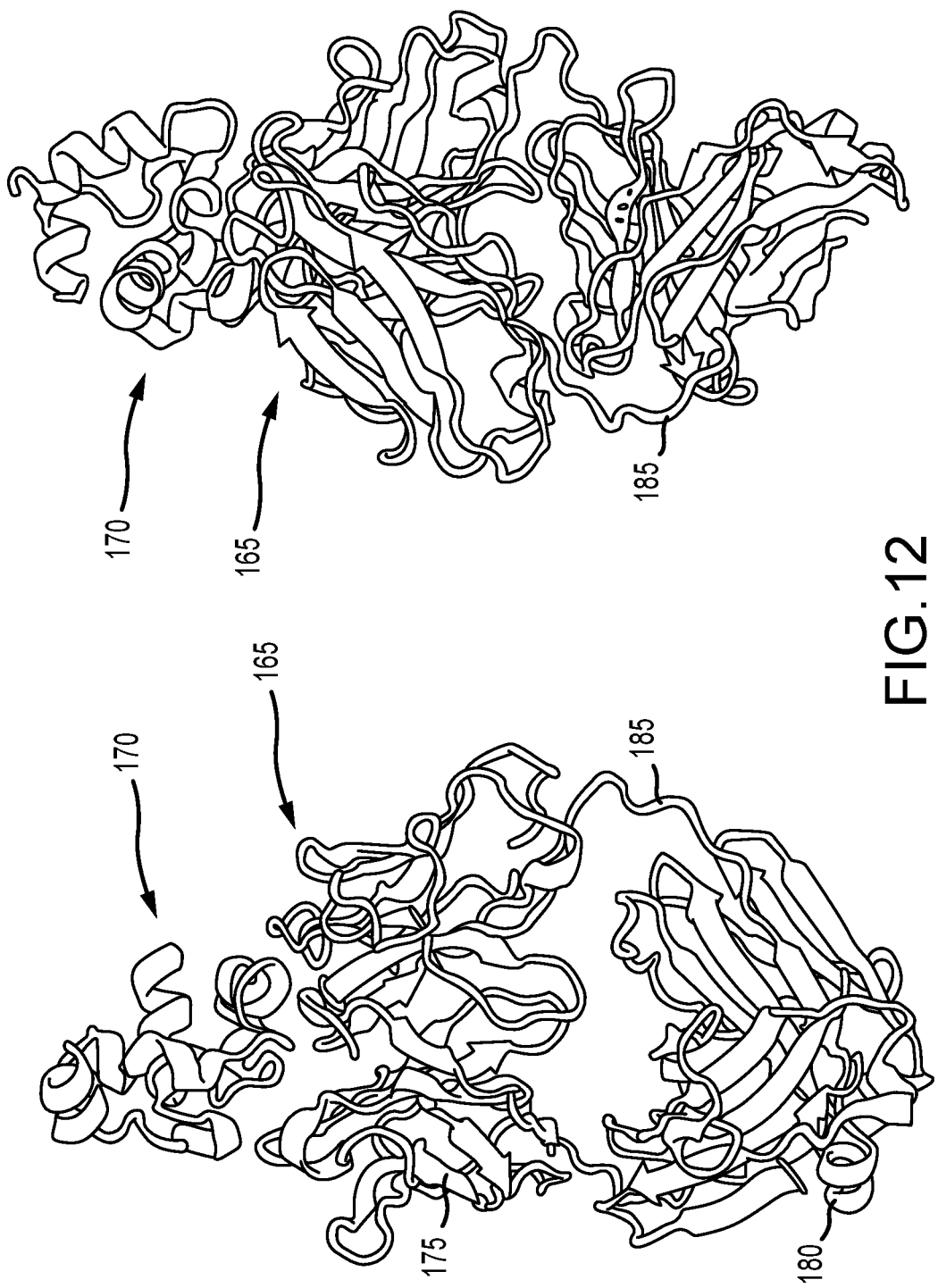
FIG. 12 illustrates a probe structure view of a binding probe that is an antibody Fab fragment, and its binding target the lysozyme protein, illustrating the presence of alpha-helix, beta-sheet, and connecting loop structures.

In various embodiments, a molecular circuit sensor comprises a Fab antibody binding domain. FIG. 12 shows a representative Fab binding probe, this one being a Fab domain that binds the lysozyme protein as a target. FIG. 12 illustrates a ribbon diagram of the binding probe structure 165, from two different views, with the binding probe engaged with its lysozyme target 170 (displaced above it). The binding probe structure contains beta sheets 175 and alpha helixes 180 as well as a loop structure 185. The binding probe in this case consists of heavy and light chain proteins complexed together. The secondary structure and tertiary structure of the Fab domain are depicted in FIG. 12. In the course of the Fab binding its target, these structural features engage in electrical, chemical, mechanical and conformational perturbations, and wiring to these features within an electrical circuit can transduce these perturbations into measured signals.

Figure 13:
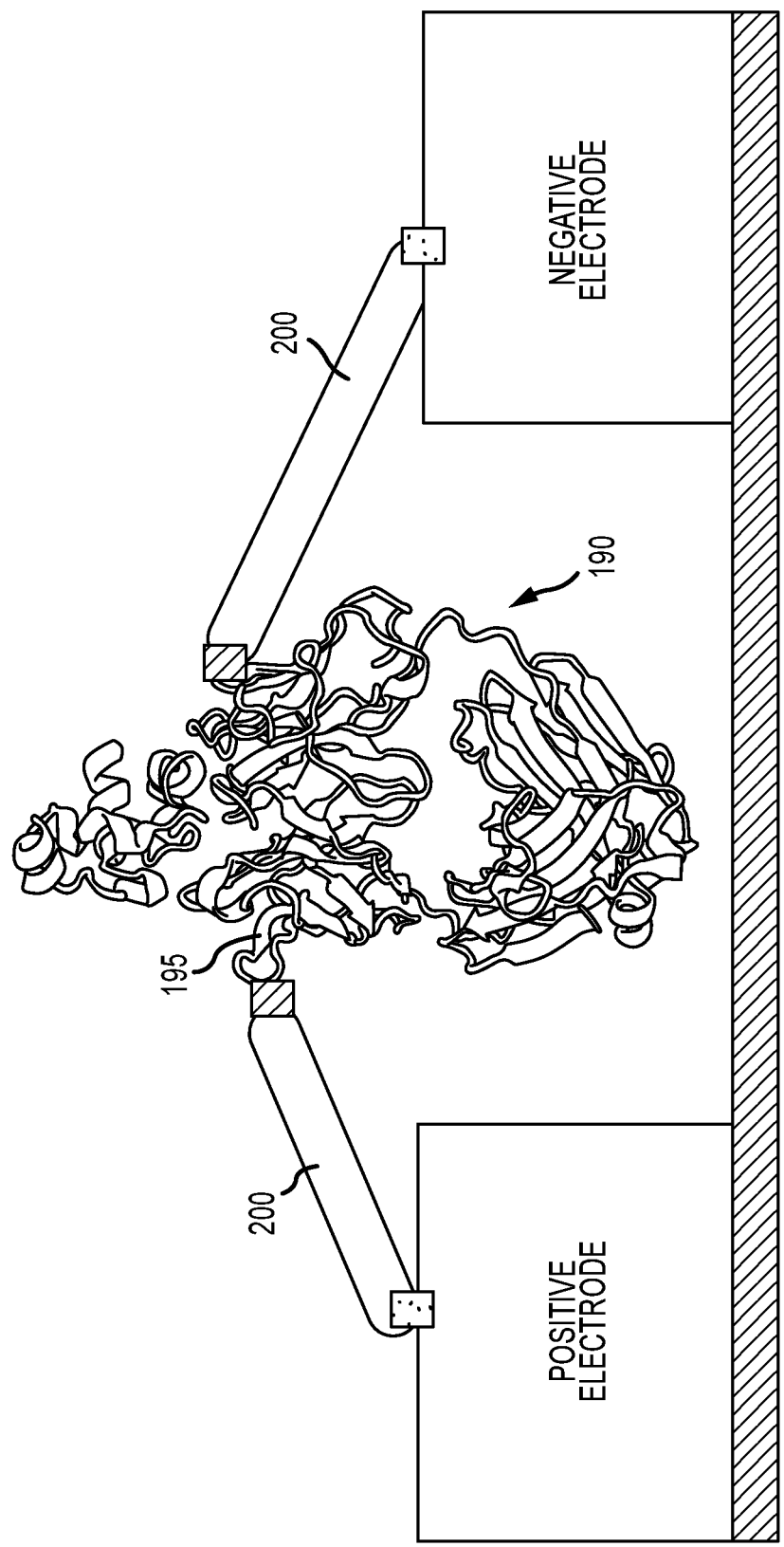
FIG. 13 illustrates a schematic of a Fab binding probe, directly wired into the current path of a circuit, in accordance with various embodiments, wherein specific beta-sheets are used for the contacts, and molecular arms provide coupling to the electrodes.
Figure 14:
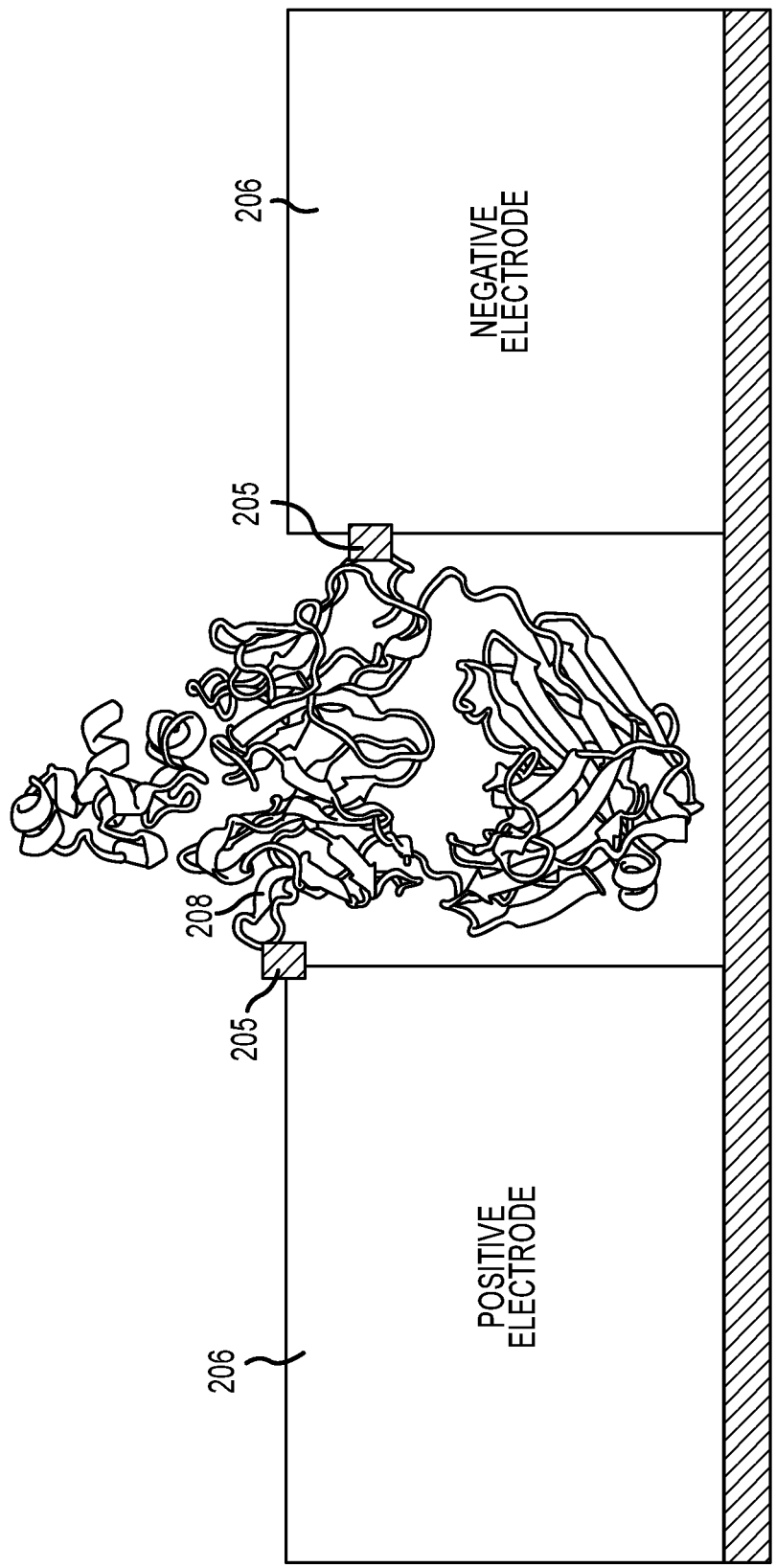
FIG. 14 illustrates a schematic of a Fab binding probe, directly wired into the current path of a circuit, in accordance with various embodiments, wherein specific beta-sheets are used for the contacts, and the probe directly couples to the electrodes without the use of arm molecules.

FIG. 13 shows an embodiment where the Fab binding probe 190 is wired as an essential conduction path, and specifically wired to the ends of beta-sheets 195 on the heavy and light chains that are complexed together to provide part of the interaction that holds the heavy and light chains together. The arms 200 indicated in FIG. 13 may comprise double stranded oligonucleotides, terminated with a maleimide, which couples to a cysteine genetically engineered into a precise location in a mutant form of the Fab domain. In another embodiment, the arms comprise a protein alpha-helix terminated with a maleimide which couples such a cysteine FIG. 14 illustrates an alternative embodiment where the mutant Fab of FIG. 13 is directly conjugated 205 to the electrodes 206, coupling to the internal beta sheet 208, without the use of connecting arms. This coupling can be achieved, for example, by utilizing gold electrodes, and a gold-binding peptide (GBP) with a maleimide terminus, such that the maleimide conjugates the GBP to the mutant Fab at the cysteine sites described above, and the GBP conjugates to the gold electrode, thereby wiring in the Fab via these two cysteine sites. Other embodiments of direct maleimide-mediated conjugation to the electrodes are obtained by using conjugating groups having the form X-maleimide bonded to the cysteines on the Fab, such that X is a group that then binds to the electrode surface.

Figure 15:
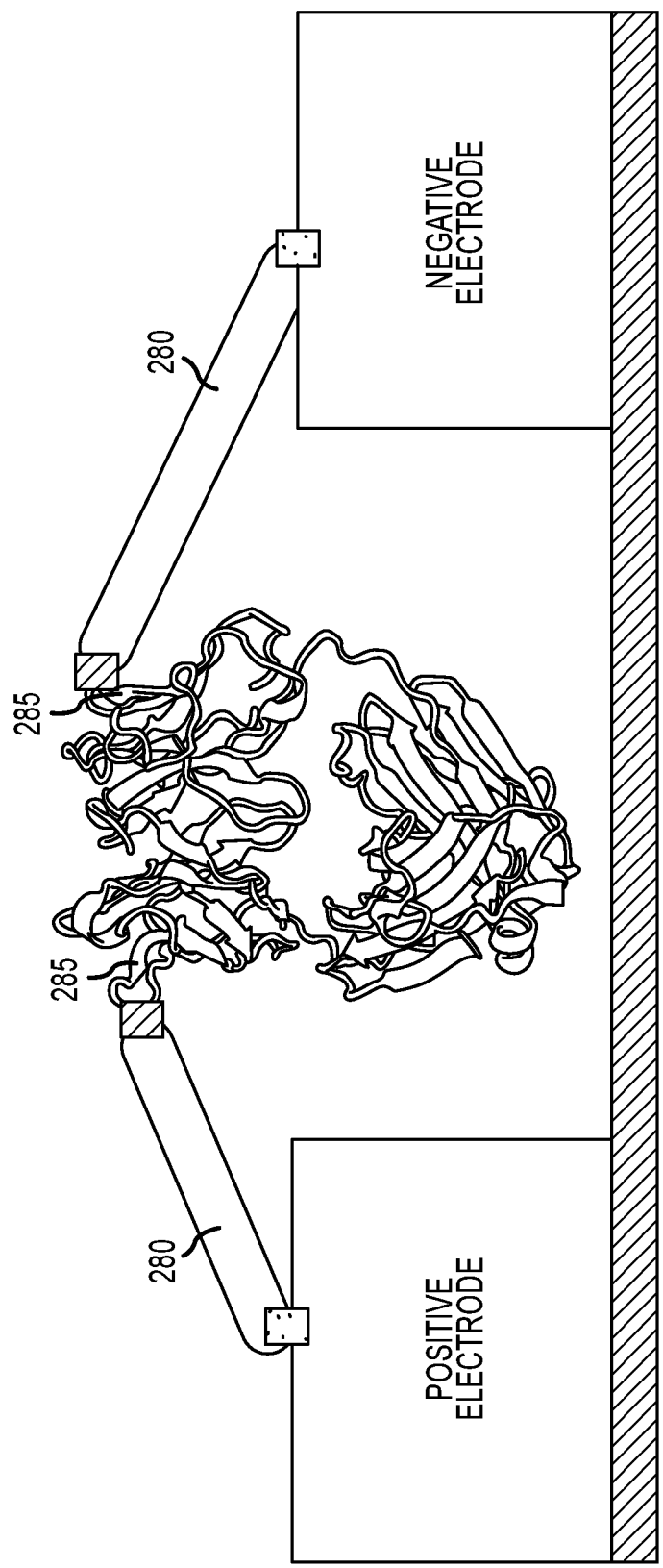
FIG. 15 illustrates a schematic of an Fab binding probe directly wired into the current path of a circuit, in accordance with various embodiments, wherein arms are wired to the points that undergo relative motion when Fab binds to its target epitope.

FIG. 15 illustrates an alternative embodiment, to the mutant Fab of FIG. 13 in which connecting arms 280 are wired to two points on internal beta-sheets 285. In embodiments, these two points have relative motion during probe binding activity that results in conformational changes of the binding probe. This relative motion can result in changes in tension and conductivity of the connecting arms.

Figure 16:
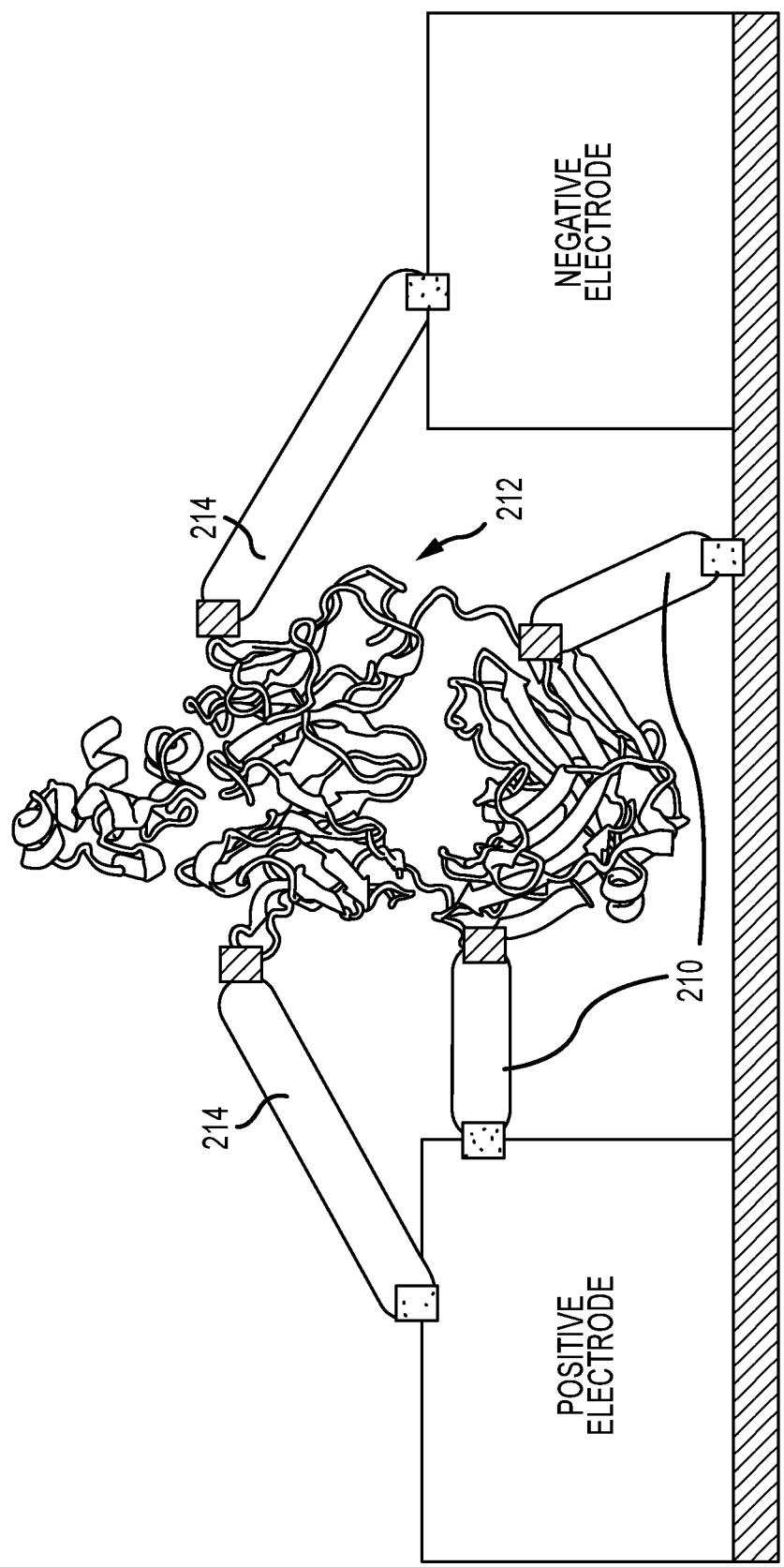
FIG. 16 illustrates a schematic of an Fab domain directly wired into the current path of a circuit, and where additional connecting arms are wired to provide stabilization and fixed spatial orientation.

FIG. 16 illustrates an embodiment in which multiple arms (a lower pair 210 and an upper pair 214) are used to wire up the Fab 212 as an essential conducting path, as well as to stabilize its position and orientation relative to the electrodes and substrate. The lower pair of arms indicated can be either conducting or insulating, in accordance with various embodiments.

In various embodiments, a circuit comprises a binding probe wired in as an essential conduction path. The circuit may comprise first and second wiring points, connecting to a first and a second electrode such as a positive electrode and a negative electrode.

In various embodiments, the circuit may further comprise at least one arm molecule having two ends, one end bonded to the binding probe and the other end bonded to at least one of the electrodes, wherein the at least one arm molecule acts as an electrical wire between the binding probe molecule and at least one of the electrodes. Such an arm molecule may be selected from the group consisting of a double stranded oligonucleotide, a peptide nucleic acid (PNA) duplex, a PNA-DNA hybrid duplex, a protein alpha-helix, a graphene-like nanoribbon, a natural polymer, a synthetic organic molecule e.g. a synthetic polymer, and an antibody Fab domain. In other examples, the binding probe is wired directly to the electrodes without the use of any arm molecules. The wiring may be to an internal structural element in the binding probe, such as an alpha-helix, or a beta sheet, or multiple such elements in series, or in spatial proximity.

In various embodiments, a circuit comprises a binding probe wired at points that undergo relative conformational change. In certain aspects, arms comprise molecules that have a tension dependent conductivity. In other examples, arm molecules may have torsion or twist dependent conductivity. Additional wiring points may be used to couple the binding probe at additional sites.

In various embodiments, a circuit comprises an antibody or antibody Fab domain, such as for example, the Fab fragment binding lysozyme, wherein the wiring is major internal beta-sheets that directly interact internal to the protein structure. Such connection may rely on the placement of genetically engineered cysteines at or near these amino acid positions, or genetically engineering in other conjugation groups at specific sites. Circuits comprising an antibody Fab may be used to detect the presence of the antigen corresponding to the antibody.

A circuit in accordance to various embodiments of the present disclosure, comprising an antibody Fab domain, may be exposed to a solution potentially containing the corresponding antigen, and may be used to detect the presence of, or concentration of, the antigen.

The connection between the binding probe and at least one of the positive electrode and negative electrode may comprise any one of: a native cysteine, a genetically engineered cysteine, a genetically engineered amino acid with a conjugation residue, or a genetically engineered peptide domain comprising a peptide that has a conjugation partner. In certain aspects, the wiring is to points on a binding probe where such points undergo relative motion in excess of 0.5 nm as the binding probe engages its target. In other aspects, the binding probe is engineered to have extended domains that produce a greater range of relative motion as the binding probe engages its target. For example, conformation changes in a probe may be accentuated by extending various domains in the probe. A binding probe may also be engineered to have additional charge groups that variably influence the internal conduction path as the binding probe engages its target.

In various embodiments, a circuit is exposed to a solution comprising the targets of the binding probe. In some cases, the binding probe is a genetically modified form an antibody, antibody Fab domain, or an aptamer. In other examples, a circuit is exposed to one or more of the conditions of: a buffer of reduced ionic strength, specific applied voltage on the primary electrodes, a gate electrode voltage, or voltage spectroscopy or sweeping applied to the primary electrodes or gate electrode.

Figure 17:
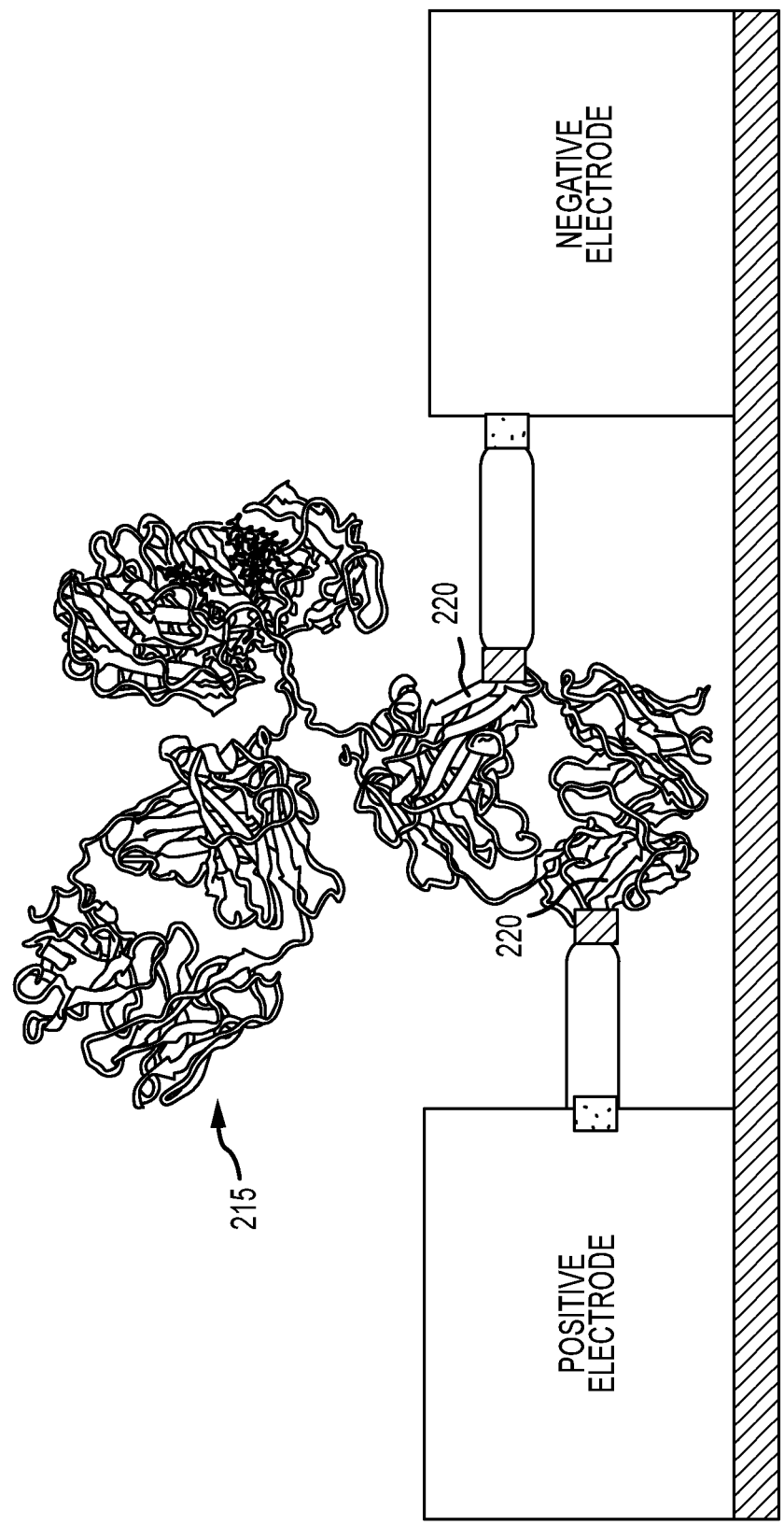
FIG. 17 illustrates a schematic of an entire IgG antibody molecule directly wired into the current path of a circuit, in accordance with various embodiments, wherein specific beta-sheets are used for the contacts, and molecular arms provide coupling to the electrodes.

In various embodiments, the binding probe may be an entire IgG antibody molecule 215, as indicated in FIG. 17, with wiring such as to the internal beta-sheets 220, as shown. Such a molecule could be a native form or a genetically engineered mutant form.

Figure 18:
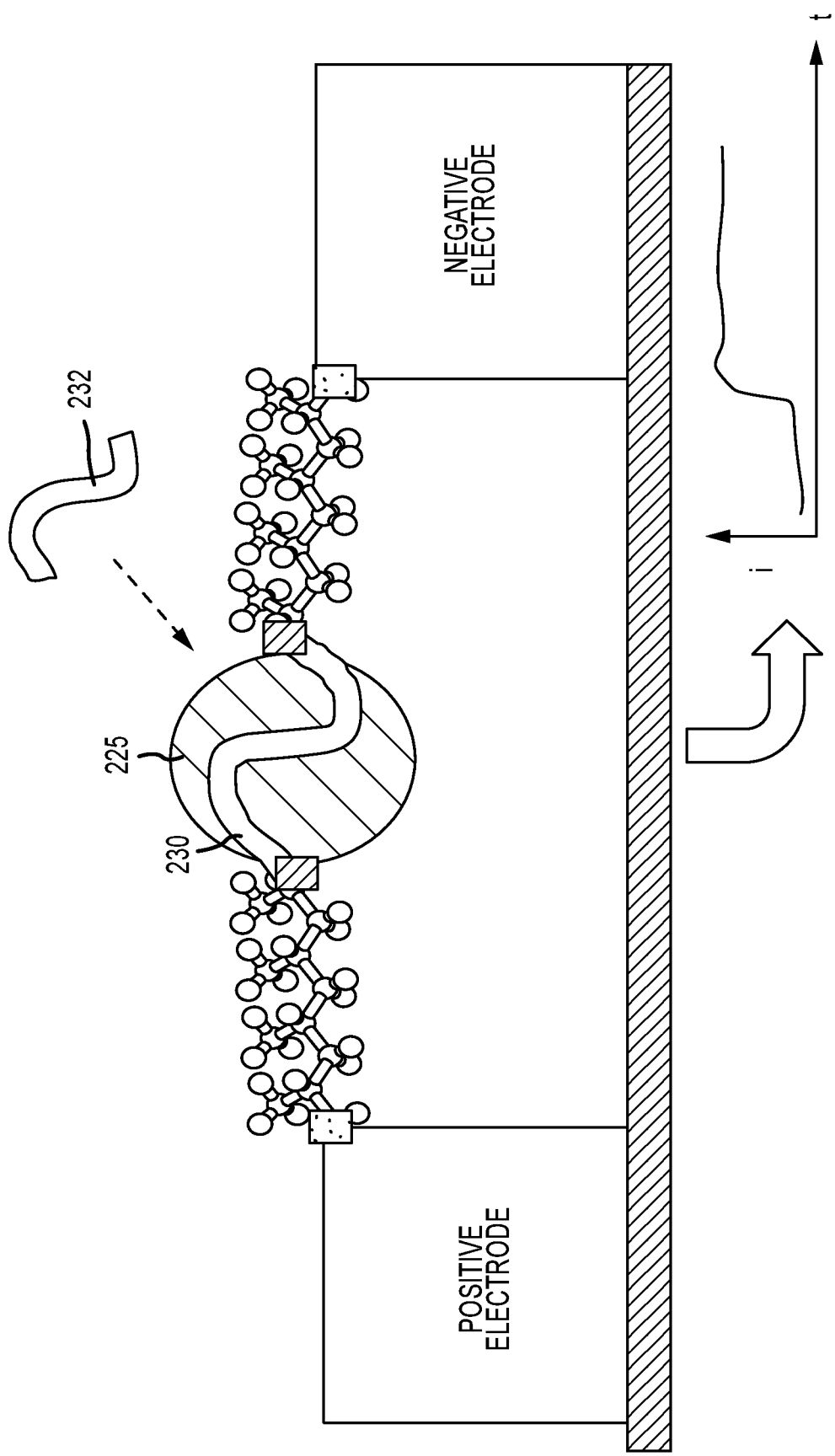
FIG. 18 illustrates a binding probe that is wired directly into the current path, in accordance with various embodiments, wherein the binding probe comprises a linear molecule that binds to a target, and arms are wired at or near the termini of the linear molecule, to complete the circuit with the electrodes.
Figure 19:
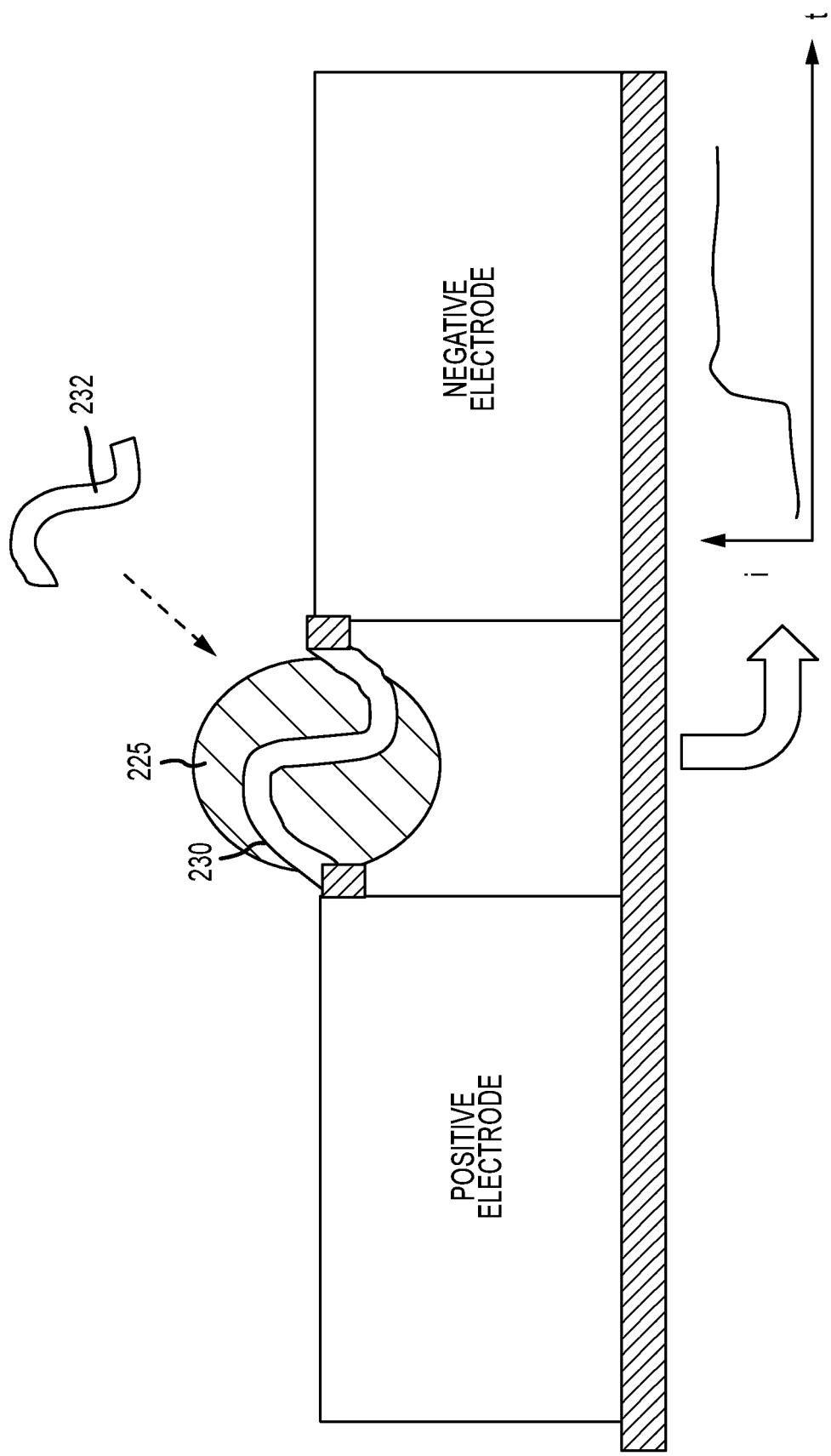
FIG. 19 illustrates a binding probe that is wired directly into the current path, in accordance with various embodiments, wherein the binding probe comprises a linear molecule that binds to a target, and the electrodes are wired directly at or near the termini of the linear molecule.
Figure 20:
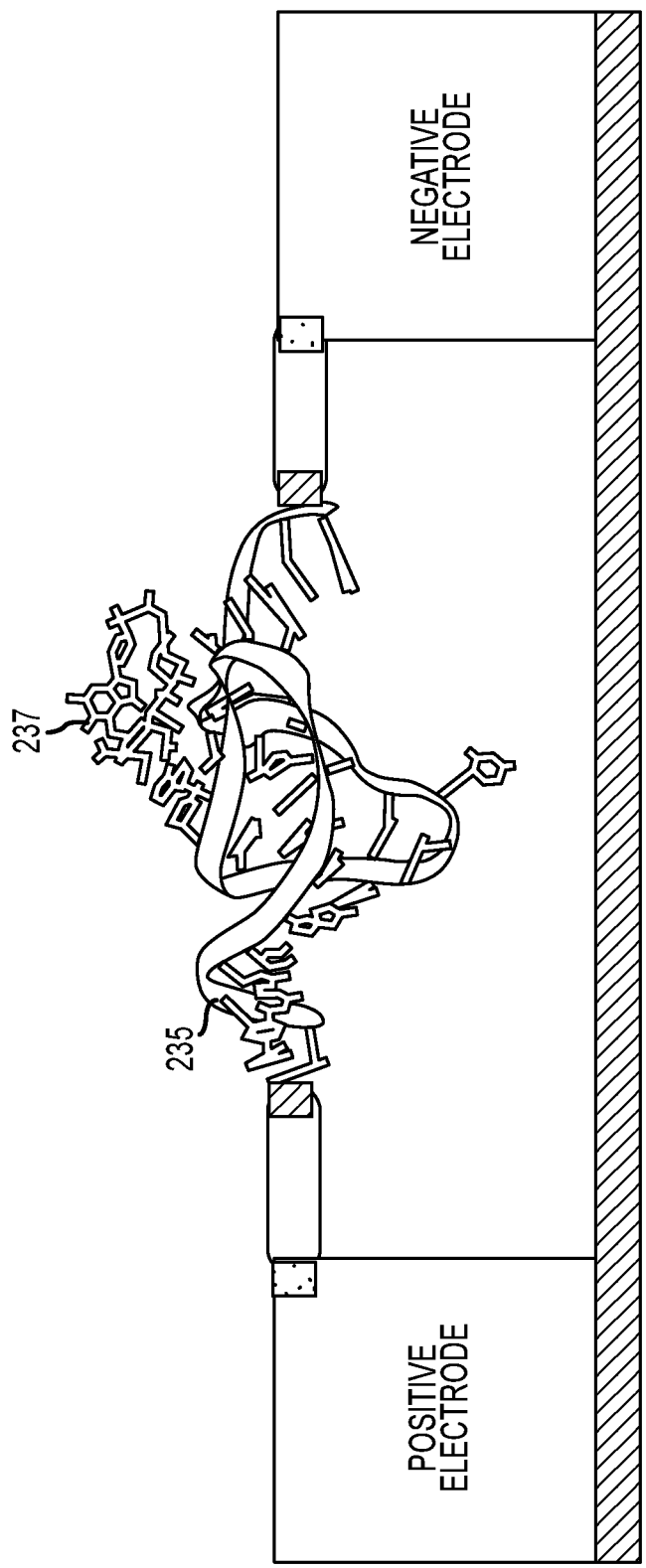
FIG. 20 illustrates an aptamer binding probe, that is wired directly into the current path, in accordance with various embodiments, wherein the aptamer shown is a single stranded DNA or RNA or other XNA nucleic acid analog oligomer, and the arms are wired at or near the termini of this linear molecule, to complete the circuit with the electrodes.
Figure 21:
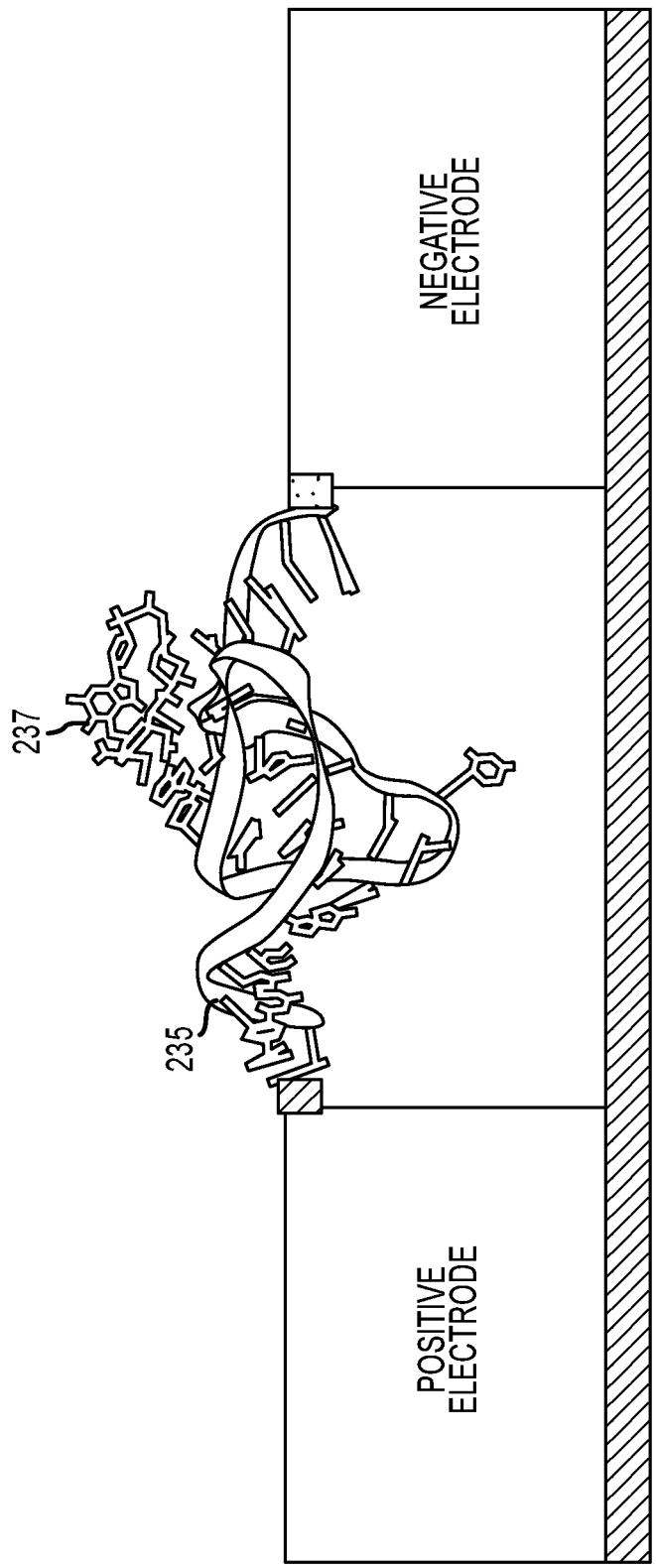
FIG. 21 illustrates an aptamer binding probe, that is wired directly into the current path, in accordance with various embodiments, wherein the aptamer is a single stranded DNA or RNA or XNA, and the electrodes are directly wired at or near the termini of this linear molecule.

In various embodiments, as indicated in FIGS. 18 and 19, the binding probe 225 may comprise a linear molecule 230 that has a binding target 232. In various embodiments, as indicated in FIGS. 20 and 21, this linear molecule could be an aptamer 235, which is typically a single strand of DNA, RNA, or XNA (nucleic acid analogue oligomer) or an amino acid peptide that binds to a specific molecular target, often a small molecule, such as vitamin B12 237 as indicated in FIGS. 20 and 21. Such aptamers can be designed or selected to bind to specific molecular targets, and a great diversity of target molecules can have cognate, specific aptamer binding probes. Thus aptamers constitute one large, important family of binding probes, somewhat analogous to antibodies in their potential for diversity and specificity, based on a standard underlying molecular framework.

Figure 22:
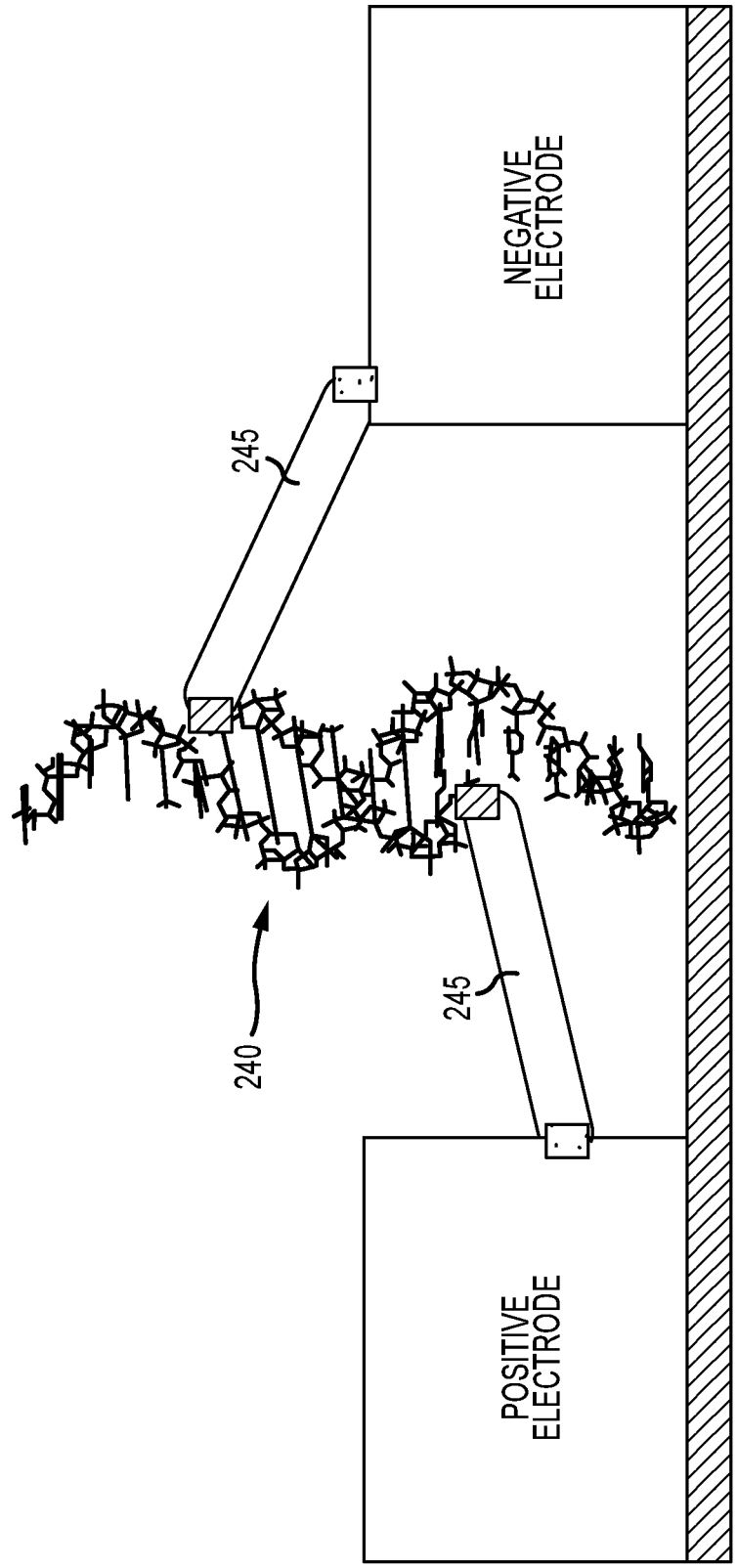
FIG. 22 illustrates a schematic of a nucleic acid hybridization binding probe molecule, composed of single stranded RNA or DNA or other XNA nucleic acid analog oligomer, directly wired into the current path of a circuit, in accordance with various embodiments, wherein sites at or near the termini of the single strand are conjugated to molecular arms provide coupling to the electrodes.
Figure 23:
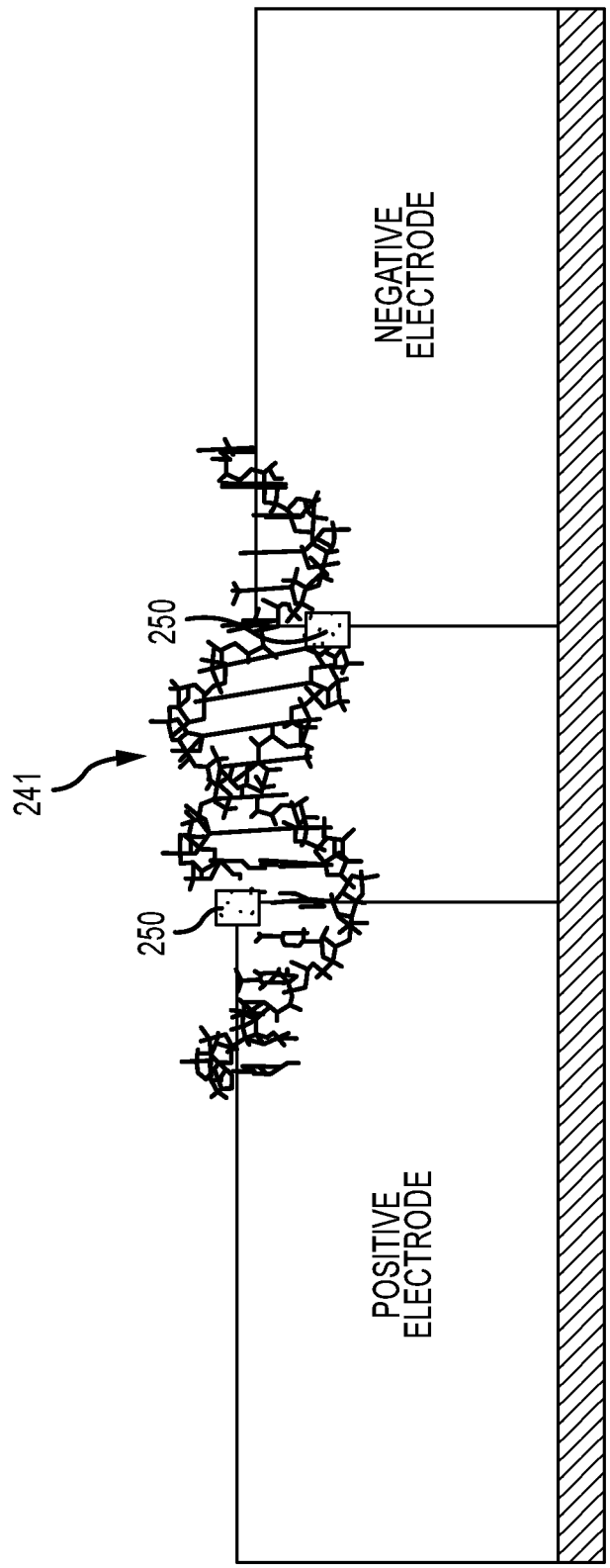
FIG. 23 illustrates a schematic of a nucleic acid hybridization binding probe molecule, composed of single stranded RNA or DNA or other XNA nucleic acid analog oligomer, directly wired into the current path of a circuit, in accordance with various embodiments, wherein sites at or near the termini of the single strand are directly conjugated to electrodes.

In other various embodiments, as indicated in FIGS. 22 and 23, the linear molecule component indicated in FIGS. 18 and 19 may comprise a single stranded DNA, RNA or XNA hybridization probe 240. Such probes specifically target DNA or RNA target molecule, based on the complementary base pairing bonds, A:T and G:C, familiar from the duplex structure of DNA. Thus the single stranded probe sequence binds to a complementary target sequence and forms a duplex "hybrid" molecule, typically with a double helix structure. Any DNA or RNA molecule that contains the complementary sequence tract is a binding target. Such hybridization probes are extensively used in classical assays such as Southern blots, and are also the basis for the widely used DNA microarray technology. Such hybridization probes are typically oligomers that are 8 to 200 bases in length or 16 to 90 bases in length. FIG. 22 illustrates how such a hybridization probe can be wired into the circuit with arms 245. FIG. 23 illustrates how such a hybridization probe can be wired directly into the circuitry without arms, with the conjugation points 250 being at or near the termini of the linear binding probe molecule. In particular, because the conductivity of single stranded and double stranded nucleic acid molecules are very different, this is a highly sensitive sensor for detecting the hybridization event, which results in the conversion from single to double strand molecules. This provides the basis for a sensor that can be used to detect the presence or absence of a specific DNA or RNA fragment, and to infer the concentration of such target molecules, even in a complex solution potentially containing diverse DNA and RNA fragments and other molecular species.

Figure 24A:
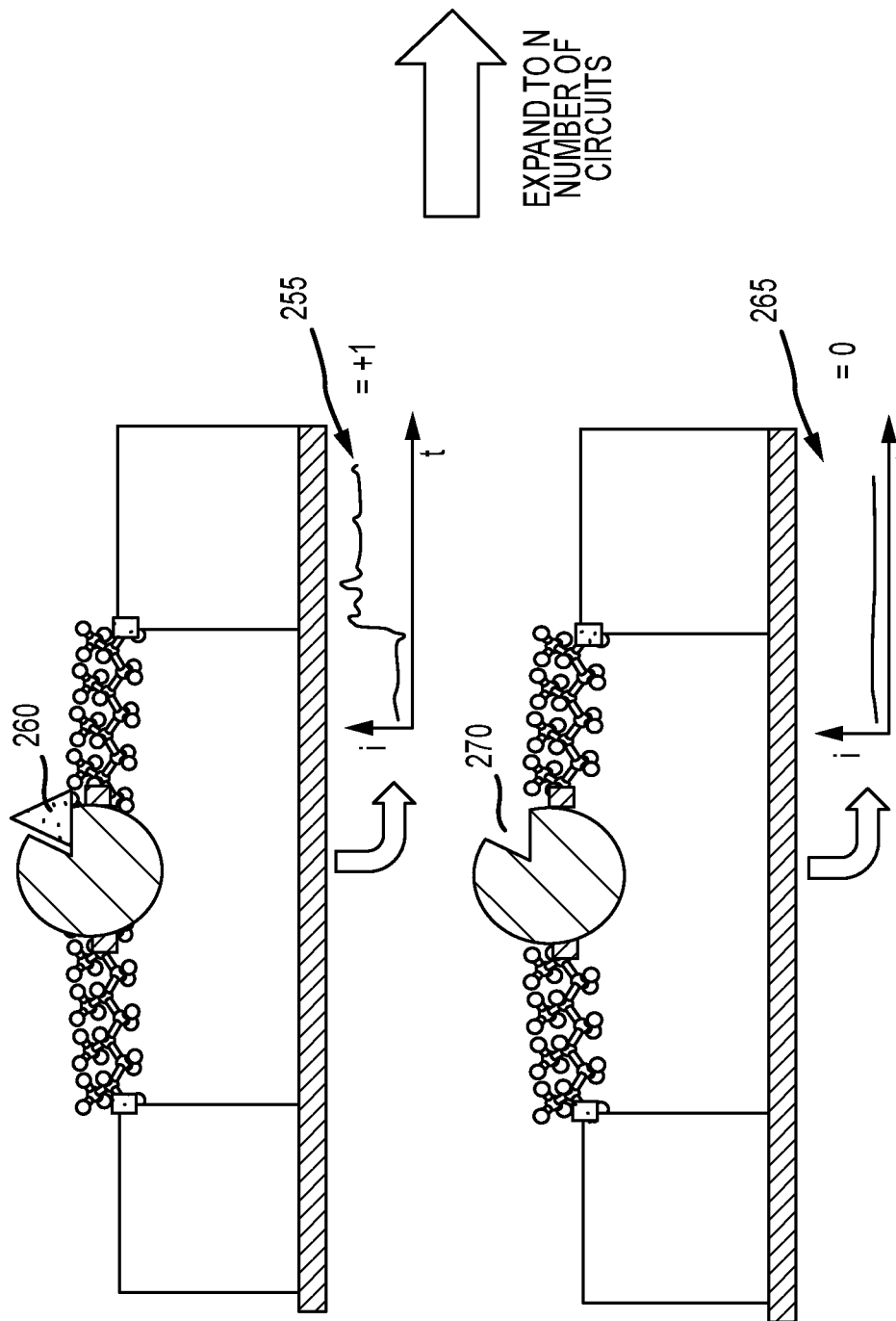
FIGS. 24A and 24B illustrate a method of making a concentration measurement using a binding probe sensor 5 circuit, wherein N instances of the sensor are exposed to a test solution and allowed to detect targets, and results are tallied to obtain a correlate of concentration.
Figure 24B:
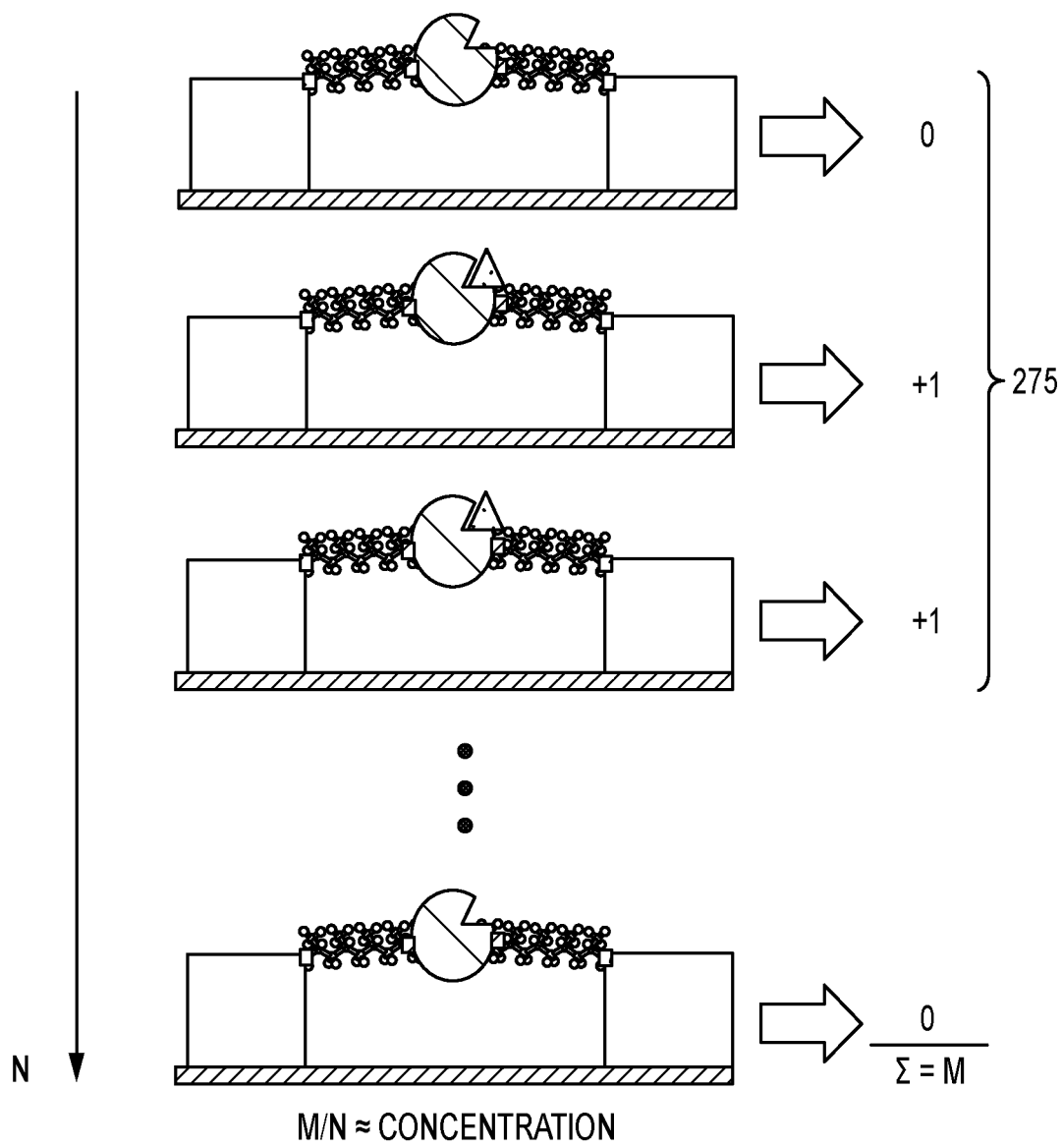

Furthermore, while a single instance of this sensor provides detection of the presence or absence of a single target molecule, the multiple application of this can be used to obtain information on the concentration of an analyte in a test solution. One embodiment of such a method is illustrated in FIG. 24A, where the electrical signal 255 indicating a target binding 260 during a measurement time period is considered a +1 count, and an electrical signal 265 with no observation of target binding 270 during the time period is considered a 0 count. As shown in FIG. 24B, the application of a large number of instances of such a measurement on a test solution, either done serially with one sensor, or in parallel with many sensors, or any combination of these, and tallying the total number of detection counts 275 over the observation time period, provides for a measure of the concentration of the target analyte, such as is summarized, for example, in the ratio M/N of the number of detection counts M, and the number of effective total sensor trials, N. The analyte concentration will correlate with this overall rate of detection in such assay, to provide a qualitative measure of concentration, and this correlation could further be calibrated to provide a quantitative measure of concentration, and this quantitative measure can further have a statistical confidence interval estimated, based on M and N and the calibration data. In certain embodiments, a large number of instances of the sensor are applied entirely in parallel to achieve this measurement. In a further embodiment, such sensors reside on a sensor array electronic measurement chip, such as a CMOS chip, with an array of sensor pixel electronic elements, each such pixel element monitoring the electrical signal from a single binding probe molecular circuit. Such a chip may be provided with in an instrument that facilitates the exposure of a liquid test sample to the chip sensors, and the capture and processing of the measured signal data. In a non-limiting embodiment, the samples may also be encoded with a traceable ID or barcode, in such a way that a multiplicity of samples can be provided to the instrument, for efficient multi-sample testing. Many such encodings are known, and may include the use of separately coded wells or tubes, or the use of detectible molecular barcodes or labels applied to individual samples, which are then pooled into a single test sample. Detection assays such as this, using binding probe molecular circuits, provide alternatives to classical, well-known qualitative and quantitative binding assays such as the ELISA (antibody-antigen binding), the Southern Blot (DNA-DNA binding), the Northern Blot (DNA-RNA binding), the Western Blot (protein-protein binding), and DNA microarrays (DNA-DNA and DNA-RNA binding), and other forms of microarrays.

In certain examples, a method of performing a binding detection assay is disclosed. The method comprises: providing a binding probe-based molecular circuit having spaced-apart positive and negative electrodes and a binding probe molecule connected to both the positive and negative electrodes to form a conductive pathway between the electrodes; initiating at least one of a voltage or a current through the circuit; exposing the circuit to a solution potentially containing the target molecule; and measuring electrical signals through the circuit as the binding probe binds a target, wherein the electrical signals are processed to identify features that provide information on the proper binding of the probe to its target.

In other aspects, a method of molecular detection is disclosed. The method comprises: (a) providing a binding probe-based molecular circuit having spaced-apart positive and negative electrodes, a binding probe molecule connected to both the positive and negative electrodes to form a conductive pathway between the electrodes, and a gate electrode; (b) initiating at least one of a voltage or a current through the circuit; (c) exposing the circuit to at least one of: a buffer of reduced ionic strength, a specific applied voltage on the primary electrodes, a gate electrode voltage, or voltage spectroscopy or sweeping applied to the primary electrodes or gate electrode; and (d) measuring an electrical change in the circuit.

Binding probe-based molecular sensors and methods of making and using same are provided. References to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a molecule, composition, process, method, or device that comprises a list of elements does not include only those elements but may include other elements not expressly listed or inherent to such molecules, compositions, processes, methods, or devices.

We claim:

1. A circuit comprising:
   a first electrode;
   a second electrode spaced apart from the first electrode;
   a binding probe electrically connected to the first electrode by a first arm molecule, and electrically connected to the second electrode by a second arm molecule, to form a conductive pathway between the first and second electrodes through the binding probe;
   wherein each of the first and second arm molecules independently comprise a protein alpha-helix, a graphene nanoribbon, or an antibody Fab domain;
   wherein each of the first and second arm molecules has a first end and a second end, wherein the first end of the first arm molecule is conjugated to the binding probe and the second end of the first arm molecule is bonded to the first electrode, wherein the first end of the second arm molecule is conjugated to the binding probe and the second end of the second arm molecule is bonded to the second electrode, and wherein the first end of each of the first and second arm molecules bond are conjugated to two distinct sites on the binding probe so that a portion of the binding probe is included in the conductive pathway.

2. The circuit of claim 1, wherein the first electrode is a positive electrode and the second electrode is a negative electrode, or wherein the first electrode is a negative electrode and the second electrode is a positive electrode.

3. The circuit of claim 1, wherein at least one of the first end of the first arm molecule or the first end of the second arm molecule is conjugated to an internal structural element of the binding probe.

4. The circuit of claim 3, wherein the internal structural element is selected from the group consisting of an alpha-helix, a beta-sheet, and a multiple of such elements in series.

5. The circuit of claim 1, wherein at least one of the first end of the first arm molecule or the first end of the second arm molecule is conjugated to the binding probe at a location of the binding probe capable of undergoing a conformational change.

6. The circuit of claim 1, wherein the at least one of the first arm molecule or the second arm molecule comprises a molecule having tension, twist or torsion dependent conductivity.

7. The circuit of claim 1, wherein the binding probe comprises an antibody Fab binding domain having a heavy chain and a light chain.

8. The circuit of claim 7, wherein the circuit is usable to sense information on the presence of, or concentration of a corresponding antibody antigen in a test solution.

9. The circuit of claim 7, wherein the two distinct sites on the binding probe consist of the ends of beta-sheets on the heavy and the light chains of the antibody Fab binding domain that are complexed together to provide part of an interaction that holds the heavy and light chains together.

10. The circuit of claim 1, wherein the binding probe comprises an aptamer.

11. The circuit of claim 10, wherein the circuit is usable to sense information on the presence of, or concentration of a target molecule of the aptamer in a test solution.

12. The circuit of claim 11, wherein the circuit is usable to sense information on the presence of, or concentration of a target DNA or RNA molecule in a test solution.

13. The circuit of claim 1, wherein the binding probe comprises an immunoglobulin protein.

14. The circuit of claim 13, wherein the immunoglobulin protein is genetically modified.

15. The circuit of claim 1, wherein the binding probe comprises a nucleic acid oligomer hybridization probe.

16. The circuit of claim 1, wherein the binding probe is engineered to have additional charge groups.

17. The circuit of claim 1, wherein at least one of the first end of the first arm molecule or the first end of the second arm molecule is conjugated to the binding probe at connection points in the binding probe comprising at least one of a native cysteine, a genetically engineered cysteine, a genetically engineered amino acid with a conjugation residue, or a genetically engineered peptide domain comprising a peptide that has a conjugation partner.

18. The circuit of claim 1, further comprising a gate electrode.

19. A method of molecular detection, comprising:
providing the circuit of claim 18;
initiating at least one of a voltage or a current through the circuit;
exposing the circuit to at least one of: a buffer of reduced ionic strength, specific applied voltage on the first electrode and the second electrode, a gate electrode voltage, or voltage spectroscopy or sweeping applied to the first electrode and the second electrode, or gate electrode; and
measuring an electrical change in the circuit.

20. The method of claim 19, wherein the electrical change is processed to identify the presence of, or concentration of an antigen.

21. The method of claim 19, wherein the electrical change in the circuit may be measured as targets interact with the binding probe.

22. The circuit of claim 1, wherein the circuit resides on a sensor array electronic measurement chip with an array of sensor pixel electronic elements, said sensor pixel electronic elements monitor the electrical signal from a single binding probe molecular circuit.

23. The circuit of claim 22, wherein the sensor array electronic measurement chip comprises a CMOS chip.

24. A method of detecting the concentration of an analyte in a solution, comprising:
providing the circuit of claim 1, wherein the binding probe is capable of binding the analyte;
initiating at least one of a voltage or a current through the circuit;
exposing the circuit to the solution for a defined period of time; and
measuring electrical signals through the circuit as the binding probe engages with the analyte,
wherein the electrical signals are processed to identify features that provide information on the concentration of the analyte in the solution.

25. The method of claim 24, wherein the concentration of the analyte in solution correlates to an overall rate of detection of the analyte to provide a qualitative measure of concentration.

26. The method of claim 25, wherein the qualitative measure of concentration is calibrated to provide a quantitative measure of concentration of the analyte.

27. A method of performing a binding detection assay, comprising:
providing a binding probe-based molecular circuit having spaced-apart first and second electrodes and a binding probe molecule, wherein the binding probe is electrically connected to the first electrode by a first arm molecule, and electrically connected to the second electrode by a second arm molecule to form a conductive pathway between the first and second electrodes through the binding probe, wherein each of the first and second arm molecules independently comprise a protein alpha-helix, a graphene nanoribbon, or an antibody Fab domain, wherein each of the first and second arm molecules has a first end and a second end, wherein the first end of the first arm molecule is conjugated to the binding probe and the second end of the first arm molecule is bonded to the first electrode, wherein the first end of the second arm molecule is conjugated to the binding probe and the second end of the second arm molecule is bonded to the second electrode, and wherein the first end of each of the first and second arm molecules are conjugated to two distinct sites on the binding probe so that a portion of the binding probe is included in the conductive pathway;
initiating at least one of a voltage or a current through the circuit;
exposing the circuit to a solution potentially containing a target molecule; and
measuring electrical signals through the circuit as the binding probe binds the target, wherein the electrical signals are processed to identify structural features that provide information on the proper binding of the probe to its target.

28. The method of claim 27, wherein the electrical signals are enhanced by at least one of a buffer, a buffer additive, and temperature.

29. The method of claim 27, wherein the structural features engage in at least one of electrical, chemical, mechanical and conformational perturbations.

30. The method of claim 27, wherein the electrical signals are processed to identify a binding event between the binding probe-based molecular circuit and the target molecule.

31. The method of claim 27, wherein the binding probe is an antibody Fab binding domain.

32. The method of claim 31, wherein the two distinct binding sites on the binding probe consist of two points on internal beta-sheets that have relative motion as the binding probe binds the target.

* * * * *